(12) United States Patent  
Greenberg

(10) Patent No.: US 8,750,590 B2  
(45) Date of Patent: Jun. 10, 2014

(54) REMOVABLE HANDLE SCAN BODY FOR IMPRESSION TRAYS AND RADIOGRAPHIC TEMPLATES FOR INTEGRATED OPTICAL AND CT SCANNING

(75) Inventor: Alex M Greenberg, New York, NY (US)

(73) Assignee: Greenberg Surgical Technologies, LLC, New York, NY (US)

( * ) Notice: Subject to any disclaimer, the term of this patent is extended or adjusted under 35 U.S.C. 154(b) by 11 days.

(21) Appl. No.: 13/366,133

(22) Filed: Feb. 3, 2012

(65) Prior Publication Data

US 2012/0230567 A1    Sep. 13, 2012

Related U.S. Application Data

(60) Provisional application No. 61/439,168, filed on Feb. 3, 2011.

(51) Int. Cl.  
*G06K 9/00* (2006.01)  
*A61C 8/00* (2006.01)

(52) U.S. Cl.  
USPC .................................... 382/131; 433/201.1

(58) Field of Classification Search  
USPC ......... 382/128, 129, 130, 131, 132, 133, 134; 378/4, 8, 21–27, 38, 168, 191, 204; 433/68, 72, 141, 201.1, 213, 214  
See application file for complete search history.

(56) References Cited

U.S. PATENT DOCUMENTS

| | | | | |
|---|---|---|---|---|
| 7,097,451 | B2 * | 8/2006 | Tang | 433/76 |
| 7,762,814 | B2 * | 7/2010 | van der Zel | 433/201.1 |
| 8,602,780 | B2 * | 12/2013 | Rubbert | 433/173 |
| 2011/0008751 | A1 * | 1/2011 | Pettersson | 433/167 |
| 2012/0123576 | A1 | 5/2012 | Pettersson et al. | |

\* cited by examiner

*Primary Examiner* — Abolfazl Tabatabai  
(74) *Attorney, Agent, or Firm* — Cozen O'Connor

(57) ABSTRACT

A device for use in optical scanning and CT scanning including a radiographic template and at least one shape of known dimension (SKD). The radiographic template includes a plurality of radio-opaque markers and is configured to take an impression of at least one surface of a patient. The SKD is removably attached to the radiographic template and serves as a basis for registration of data of a CT scan of the device with data of an optical scan of the device. The device may further comprise a mounting plate. The SKD is mounted on the mounting plate such that the at least one SKD is in an exact same position with respect to surfaces in a model formed from the impression as when the impression of the patient is formed in the radiographic template.

21 Claims, 13 Drawing Sheets

REMOVABLE HANDLE SCAN BODY FOR IMPRESSION TRAYS AND RADIOGRAPHIC TEMPLATES FOR INTEGRATED OPTICAL AND CT SCANNING

RELATED APPLICATIONS

This application claims priority from U.S. Provisional Patent Application Ser. No. 61/439,168, which was filed on Feb. 3, 2011, the entire contents of which are incorporated herein by reference.

1. FIELD OF THE INVENTION

The present invention relates to dental implant and orthodontic treatment planning and in particular to the creation of integrated CT and optical scan data for dental implant and orthodontic treatment planning and the production of dental models, surgical drill templates and orthodontic aligners.

2. DESCRIPTION OF THE RELATED ART

CT scanned 3D images and virtual optically acquitted images of dentitions are conventionally registered to allow for treatment planning for the placement of dental implants and orthodontic treatment aligners. For example, U.S. Pat. Nos. 7,573,583 and 7,355,721 describe conventional imaging methods that relate to the well-known dental software E4D Compass. U.S. Pat. No. 6,319,006 relates to another conventional imaging method well-known in the dental field. U.S. Publication Nos. 2006/0291968 and 2009/0113714 and U.S. Provisional Patent Application No. 61/414,764 by the present inventor, the entire contents of which are incorporated herein by reference, disclose drilling templates and orthodontic aligners formed from conventional imaging and treatment planning methods.

These conventional methods provide for the superimposition of CT scanned 3D or virtually optically acquired images of radiographic templates and dentitions on the basis of surface-to-surface superimposition. However, these conventional methods have limitations in that they require the bonding of a shape of known dimensions (SKD) on the dentition itself as in the methods of U.S. Pat. No. 6,319,006 and U.S. Publication No. 2011/0008751 so that the dentition can be acquired by the CT and optical scans for registration. Conventional methods are thus limited by the need to apply physical markers of standardized known dimensions and shape to the teeth themselves. Moreover, these conventional methods do not provide for the creation or use of custom impression trays or standardized impression trays with modular or removable parts, let alone for impression trays or radiographic templates having removable shapes of known dimensions.

The merger of two data sets of digitized CT images involving the superimposition of a separate CT image of the radiographic template to CT bone images of the radiographic template in the patient's mouth also does not provide a sufficient level of detail and accuracy required for the production of some types of dental models, surgical drill templates and orthodontic aligners.

Furthermore, another limitation of conventional imaging methods is their dependence on surfaces of adjacent teeth for determining a dental implant trajectory.

SUMMARY OF THE INVENTION

One objective of the present invention is to provide an improved method which permits the combined registration of fiducial markers and a removable shape of known dimensions (SKD), e.g., a Lego®, to provide for the registration of data of a CT scan and data of an optical scan as an improvement over conventional methods.

A further objective of the present invention is to provide for the creation and/or use of custom impression trays or standardized impression trays with modular or removable parts, or a removable shape of known dimensions.

Another objective of the present invention is to form a template for use with an instrument to drill a hole at a location and/or for orthodontic movement of at least one tooth based on a virtual model created from the registration of data from a CT scan and data from an optical scan as an improvement over conventional methods.

Still another objective of the present invention is to avoid a reliance upon surfaces of adjacent teeth for determining a dental implant trajectory by utilizing a tooth form or dental bridge (fixed partial denture) form in coordination with underlying bony anatomy to determine the desired dental implant trajectory.

According to an example embodiment, a device for use in optical scanning and CT scanning ma include a radiographic template and at least one SKD. The radiographic template includes a plurality of radio-opaque markers and is configured to take an impression of at least one surface of a patient. The SKD is removably attached to the radiographic template and serves as a basis for registration of data of a CT scan of the device with data of an optical scan of the device.

According to another example embodiment, the device may further comprise a mounting plate. The SKD is mounted on the mounting plate such that the SKD is in an exact same position with respect to surfaces in a model formed from the impression as when the impression of the patient is formed in the radiographic template.

According to still another example embodiment, a method for producing a virtual model of a patient includes providing a radiographic template including an impression of at least one surface of the patient. The radiographic template has at least one shape of known dimensions (SKD) removably attached thereto. A model is created from the impression in the radiographic template. The radiographic template having the at least one SKD attached thereto is mounted on at least one mounting plate such that the at least one SKD is transferred to the mounting plate in an exact same position with respect to surfaces in the model as when the impression was formed in the radiographic template. The model and the SKD are optically scanned on the mounting plate without the radiographic template.

BRIEF DESCRIPTION OF THE DRAWINGS

The invention will now be described in further detail with reference to the drawings in which.

DETAILED DESCRIPTION OF THE PRESENTLY PREFERRED EMBODIMENTS

Example embodiments of the present invention utilize processes disclosed in R. Jacobs et. al., "Predictability of a three dimensional planning system for oral implant surgery", Dentomaxillofacial Rad., 1999, 28, pp. 105-111, and Van Steenberghe, "A custom template and definitive prosthesis", Int. J. Maxillofacial Implants, 2002, 17, pp. 663-670, as well as processes in U.S. Pat. No. 7,574,025, the entire contents of which are incorporated herein by reference. U.S. Pat. No. 7,574,025 discloses the use of a dual scan process of a radiographic scan appliance or template with fiducial markers for performing a scan of a radiographic template in a patient's mouth and a separate scan of the radiographic template in a Styrofoam box, thus creating two data sets that allow for the creation of an artifact corrected image. The two data sets of digitized CT images are merged in planning software with registration and superimposition of the separate image of the radiographic template to the bone images of the radiographic template in the patient's mouth. Registration is a software process whereby the separate 3D digital image of the radiographic template alone is overlaid on the 3D digital image of the radiographic template in the patient's mouth so that their outlines match in spite of artifact distortion.

Figure 1:
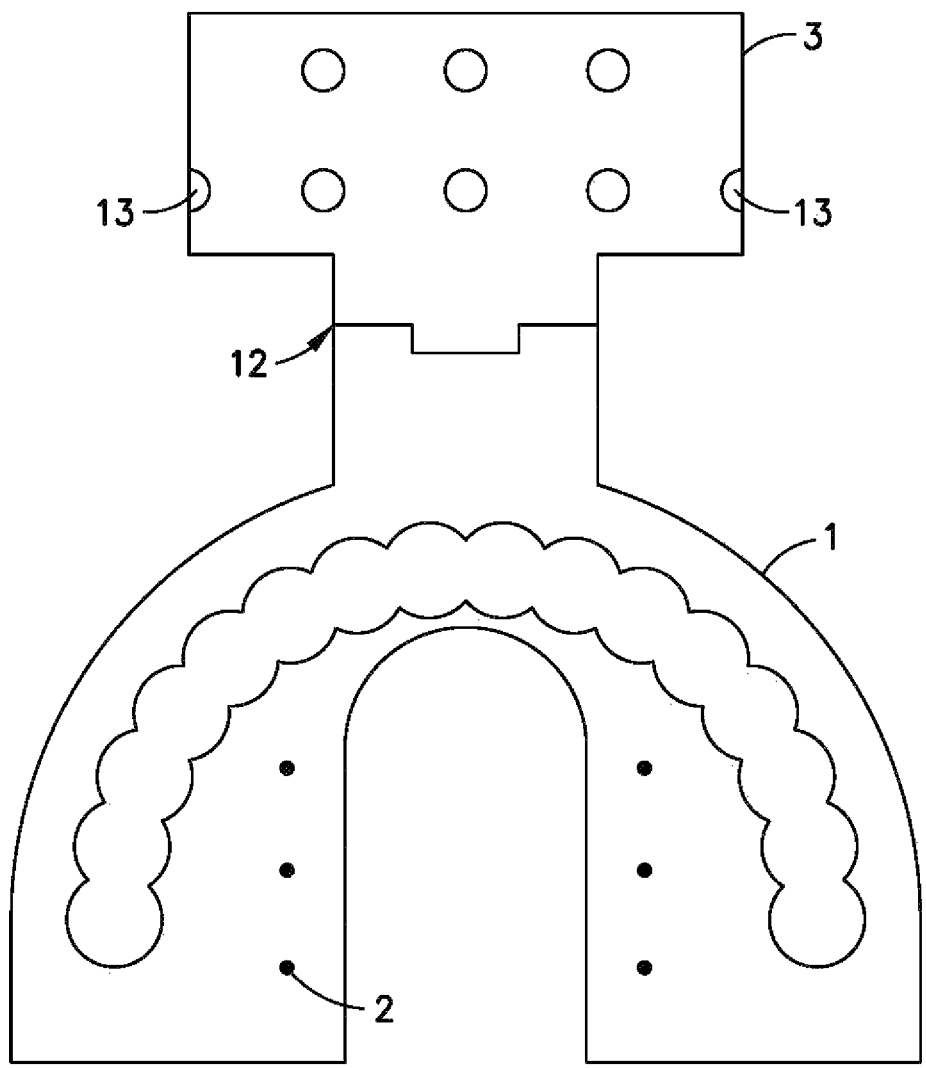
FIG. 1 shows a radiographic template according to an example embodiment.
Figure 2A:
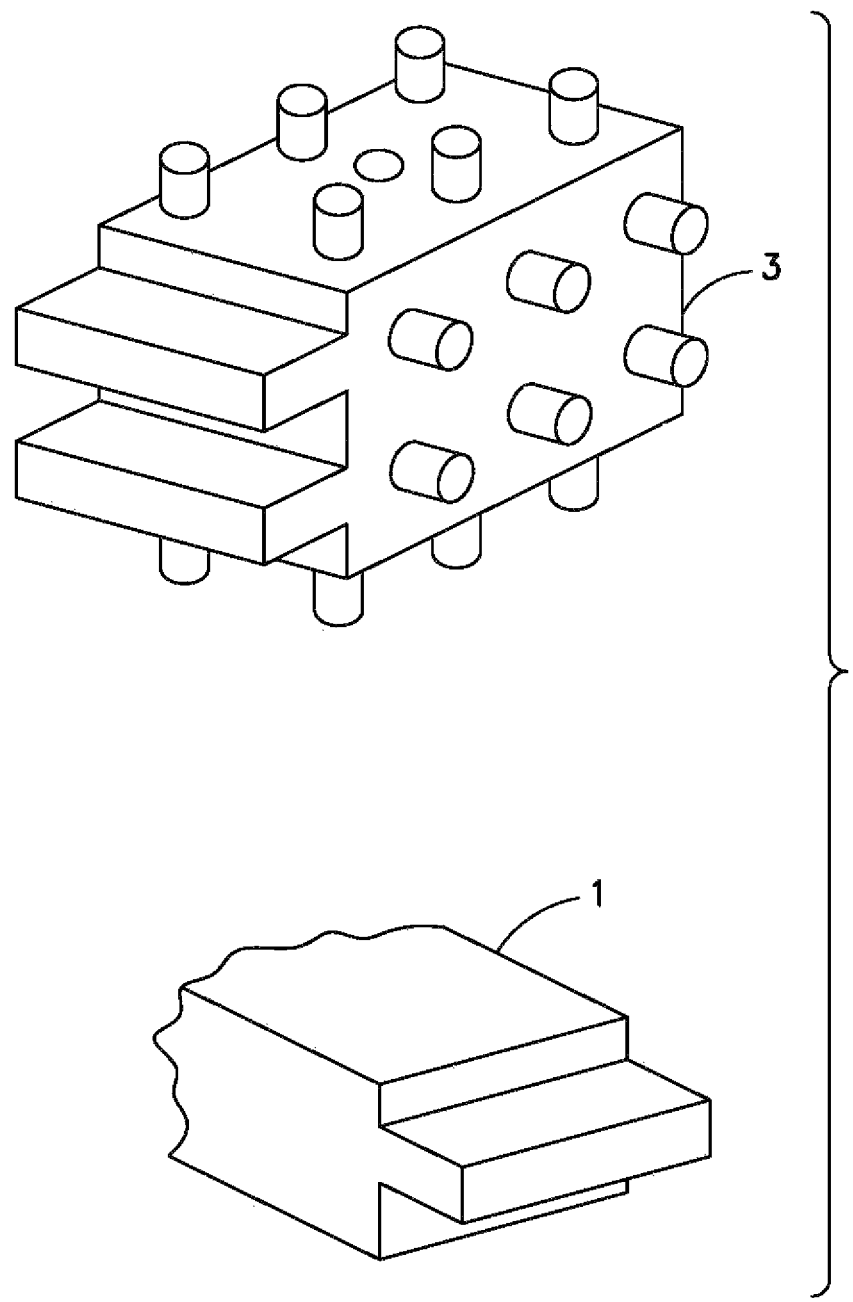
FIG. 2A shows a tray or template handle and a shape of known dimensions (SKD) according to an example embodiment.
Figure 2B:
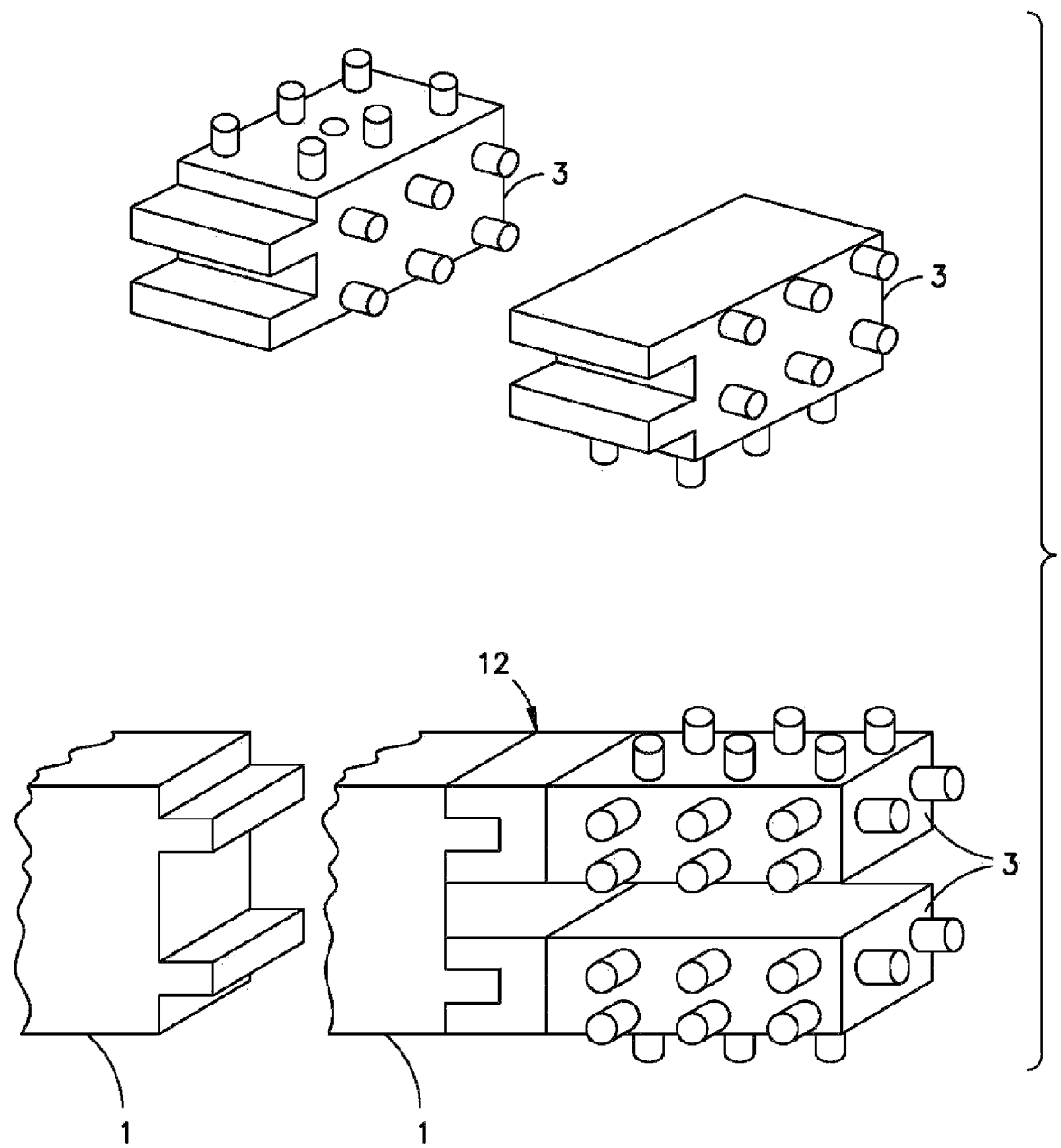
FIG. 2B shows a tray or template handle and a SKD according to another example embodiment.

FIG. 1 shows an impression tray or radiographic template 1 according to an example embodiment. The radiographic template 1 comprises fiducial markers 2, which can be made of a radio-dense or radio-opaque material, such as, metal filings, gutta-percha etc., and a removable shape of known dimensions (SKD) 3, e.g. a Lego®. The radiographic template 1 can be a standardized template manufactured from an injection-molded material, and comprises the SKD 3 removably attached thereto, e.g., as a scanbody handle, as shown in FIG. 1. The SKD 3 is thus removable from the radiographic template 1. The SKD 3 of the radiographic template 1 may extend outside the mouth or lips of a patient when the radiographic template 1 is in the patient's mouth. The radiographic template 1 may alternatively have a modular form, as disclosed in U.S. Publication No. 2006/0291968, the entire contents of which are incorporated herein in their entirety. The radiographic template 1 may be a custom radiographic template made from a malleable material. The SKD 3 can be either a positive or a negative impression depending upon the needs of the software manipulating data for the processing of digitized images in order to create the registration between a data set of a CT scan of the patient and the radiographic template 1 and a data set of a CT scan of the radiographic template 1 alone, and a separate additional registration of an optical scan of a negative impression of the radiographic template 1 including the SKD 3.

The removable scanbody or SKD 3 is attached to the standardized impression tray, the custom impression tray or the custom radiographic template serving as the radiographic template 1 by a detachable joint 12. The joint 12 may comprise a friction fit retaining element, a spring loaded retaining element, a ball bearing retaining element or various other retaining elements. The SKD 3 and radiographic template 1 may be configured in various manners to allow the SKD 3 to be removably attached to the tray or radiographic template 1. FIGS. 2A, 2B, 3A and 3B, discussed in more detail below, show various configurations of the scanbody handle or SKD 3 to the radiographic template 1.

The impression tray or radiographic template 1 is configured to take a negative impression of a patient's teeth. The negative impression of the radiographic template 1 contains occlusal surfaces of the patient's teeth in a malleable material, e.g., dental acrylic, or the impression can be a negative impression of the teeth with a material, such as, a polyether or poly vinyl siloxane, applied to the radiographic template 1 which is used as a dental impression tray. The radiographic template 1 may be standardized in different sizes to accommodate different sized mouths, e.g., in small, medium, and large sizes. The radiographic template 1 may be a "Triple Tray" or dual impression tray configured to take combined upper and lower jaw impressions as a single integrated piece or two detachable trays, with and without interocclusal acrylic, plastic or other soft materials that allow an interdigitated bite registration to be obtained.

Figure 4:
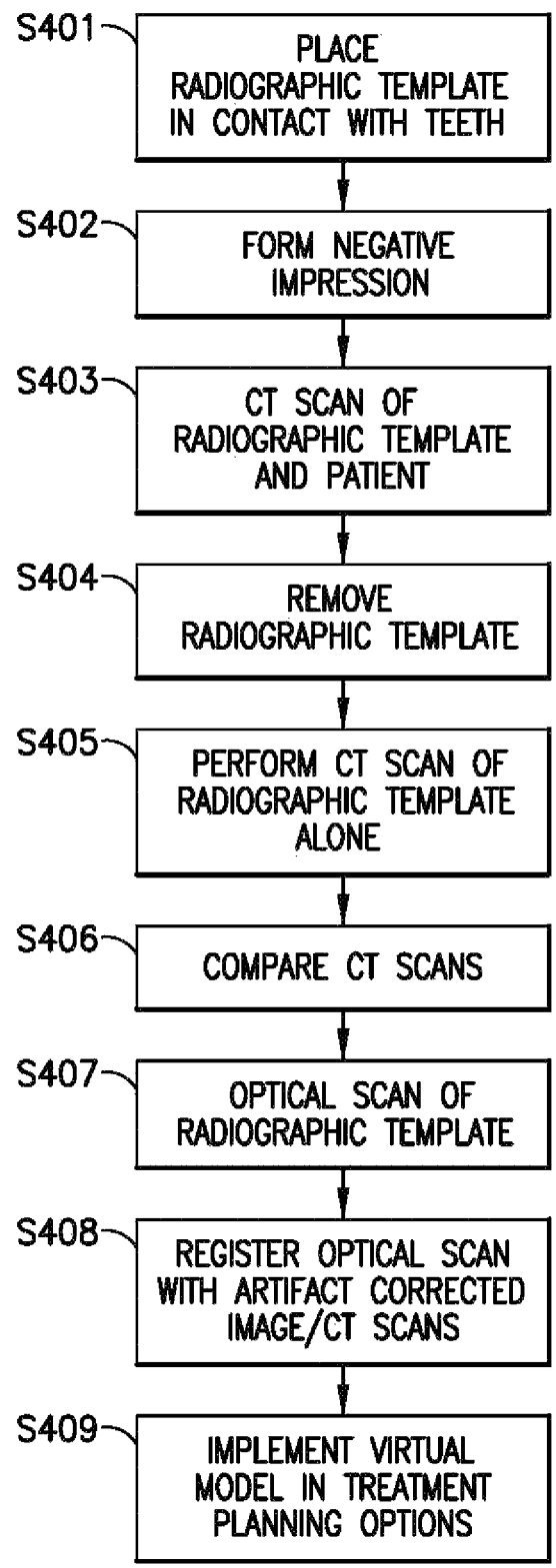
FIG. 4 is a flow chart showing steps for producing a virtual model according to an example embodiment.

FIG. 4 is a flow chart showing a method for producing an artifact corrected image which includes the registration of data from a CT scan and data from an optical scan according to an example embodiment. The radiographic template 1 is placed in contact with the patient's teeth at S401. A negative impression of the patient's teeth is formed by said radiographic template 1 at S402. A CT scan of the patient, i.e., the patient's teeth, and radiographic template 1 is performed at S403. The radiographic template 1 is removed from the patient at S404. A CT scan of the radiographic template 1 alone, i.e., apart from the teeth of the patient, is performed at S405. Registration (comparison or merger) of the data sets of the two CT scans is performed at 4306 to create an artifact corrected image. The registration may be based on the fiducial markers 2 in each of the CT scans such that the fiducial markers in the first scan are matched with the fiducial markers in the second scan in order to align the two CT scans. The registration, i.e., merger or comparison, of the two CT data sets provides an artifact corrected image to be superimposed over the bone image so that in the presence of dental restorations or fixed metal orthodontic appliances, the radiographic template 1 can be segmented in a correct relationship to the anatomic bony structures. The artifact corrected image provides for the insertion of a post segmentation functional element, such as, a dental implant trajectory that can be transformed into a shape within the radiographic template clean artifact corrected image as drill trajectory channel that will be formed as a subtraction of material in the rapid prototyping/rapid printing of the digitally created surgical drill guide template as described in U.S. Pat. No. 7,574,025. The additional matching of an optical 3D data set, as described below, provides a data set of higher accuracy as the artifact corrected image for use in the software to create a CAD/CAM surgical template, CAD/CAM dental prosthetic part fabrication and orthodontic aligner manufacturing.

The radiographic template is optically scanned by either a hand held scanner, e.g., a Sirona CEREC, 3M Lava, D4D E4D, Densys, Cadent iTero, or a desk top scanner, e.g., a 3MLava, Straumann Etkon, D4D E4D, to create a virtual negative impression of the negative impression of the radiographic template 1 at S307. A .stl file of the optically scanned virtual model of the dentition is registered with the CT scan data of the registered patient data and radiographic template and the artifact corrected radiographic template through registration based on the SKD S308. That is, the registration of the optical scan with the CT scans is based on the SKD in the optical scan and the SKD in the CT scans such that the SKD in the optical scan is aligned or matched with the SKD in the CT scans so that the optical scan can be merged with the CT scans. Accordingly, an artifact corrected image of the dentition can be represented in the combined CT and optical scans of the patient and radiographic template data, which provides a virtual model that can be used in various treatment planning options and for the production of dental models, surgical drill templates and orthodontic aligners. The combined CT and optical scans of the patient and radiographic template data advantageously provides for the merger of micron level accurate data of the teeth from the optical scan with millimeter level accurate date of the bone from the CT scans. Moreover, the need for a second scan of the radiographic template 1 may be obviated. The integrated CT scan and optically scanned data image provides for a multitude of treatment planning options for a practitioner within a virtual environment that can allow a variety of outputs through rapid manufacturing/rapid printing/rapid prototyping and computer aided design/computer aided manufacturing (CAD/CAM) manufacturing methods. The multitude of outputs can be used for the fabrication of dental implant surgical guides, jaw fracture bone plating drill guides, medical applications, such as, electrode insertion for modulation of the Sphenopalatine/nasoplatine ganglion for vascular effects as disclosed in U.S. Pat. Nos. 7,120,489 and 7,729,759, and orthodontic appliances. The fabrication processes can also be performed in modular forms. The virtual planning environment also provides for the virtual insertion of crowns, bridges, dental implant fixed and removable prostheses and their parts for the planning, fabrication, and insertion of dental prosthetics, dental implants, orthodontic aligners and any combination thereof for dental treatment. In orthognathic surgical intervention a series of presurgical, surgical and post surgical interventions can be planned and simulated virtual surgical splint can be created that is then fabricated by CAD/CAM processes. The integration of CBCT and optical scan data to create an articulated set of models for planning all aspects of orthodontics, oral and maxillofacial surgery, and creation of surgical splints for orthognathic surgery is known such as, for example, the Medicim Maxilim software.

A standardized dental impression tray or radiographic template 1 can be manufactured as a single tray, a quadrant tray or a triple tray, each type of tray having a scanbody handle. The radiographic template 1 may be fabricated in a modular manner so that an end of the radiographic template 1 that protrudes forward from a mouth of a patient has a joint 12 for attachment of the removable SKD 3 to the radiographic template 1. The joint 12 may be any male to female connection that allows for the SKD3 to be stably connected to the radiographic template 1 as a scanbody handle, and easily removed from the radiographic template 1. The SKD 3 may be 3D optically scanned from any direction, for example, from a bottom or impression side of the tray or template 1, from a top or non-impression side of the tray or template 1, or head-on, so that the entire impression tray or radiographic template 1 is scanned. The SKD 3 may have a plurality of different shapes and dimensions, either protruding from the oral cavity of the patient or remaining within the oral cavity of the patient. The tray or template 1 comprises at least three fiducial radiographic radiodense markers 2, and preferably six fiducial radiographic radiodense markers 2. The removable SKD 3 allows the SKD 3 to be reused after sterilization, which reduces the cost of manufacturing standardized impression trays that are manufactured to be disposable.

The removable SKD 3 may further comprise on a top and/or bottom or end thereof openings 13 which allow the insertion of a holding stem that permits the transfer of the SKD 3 to a mounting plate or the SKD 3 to be incorporated within a plaster dental cast or CAD/CAM manufactured dental model.

Figure 5A:
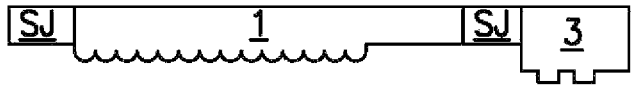
FIGS. 5A through 5G show a radiographic template with a dental model for transfer of the dental model to a base plate according to an example embodiment.
Figure 5B:
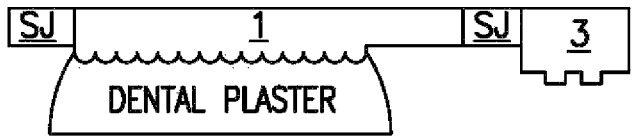
Figure 5C:
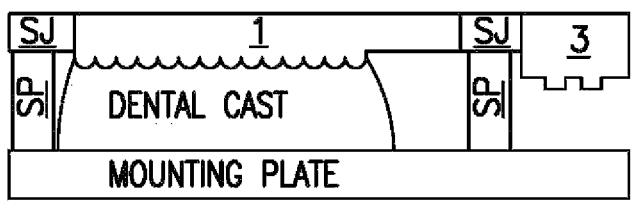
Figure 5D:
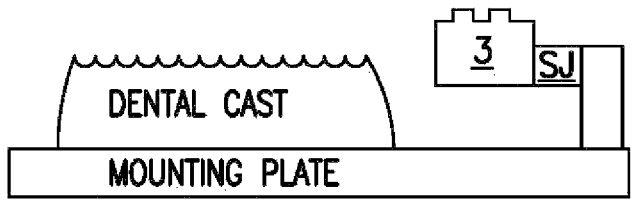
Figure 5E:
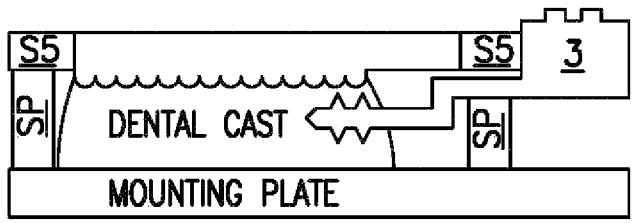
Figure 5F:
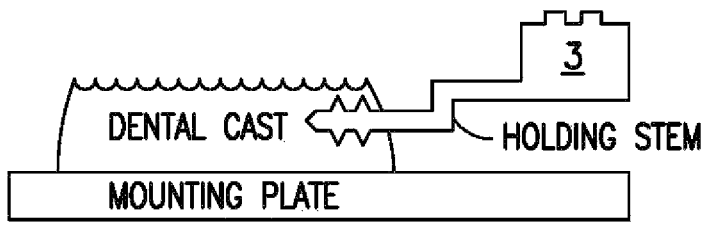
Figure 5G:
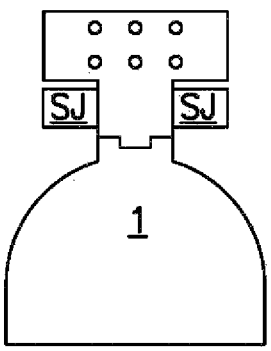
Figure 6:
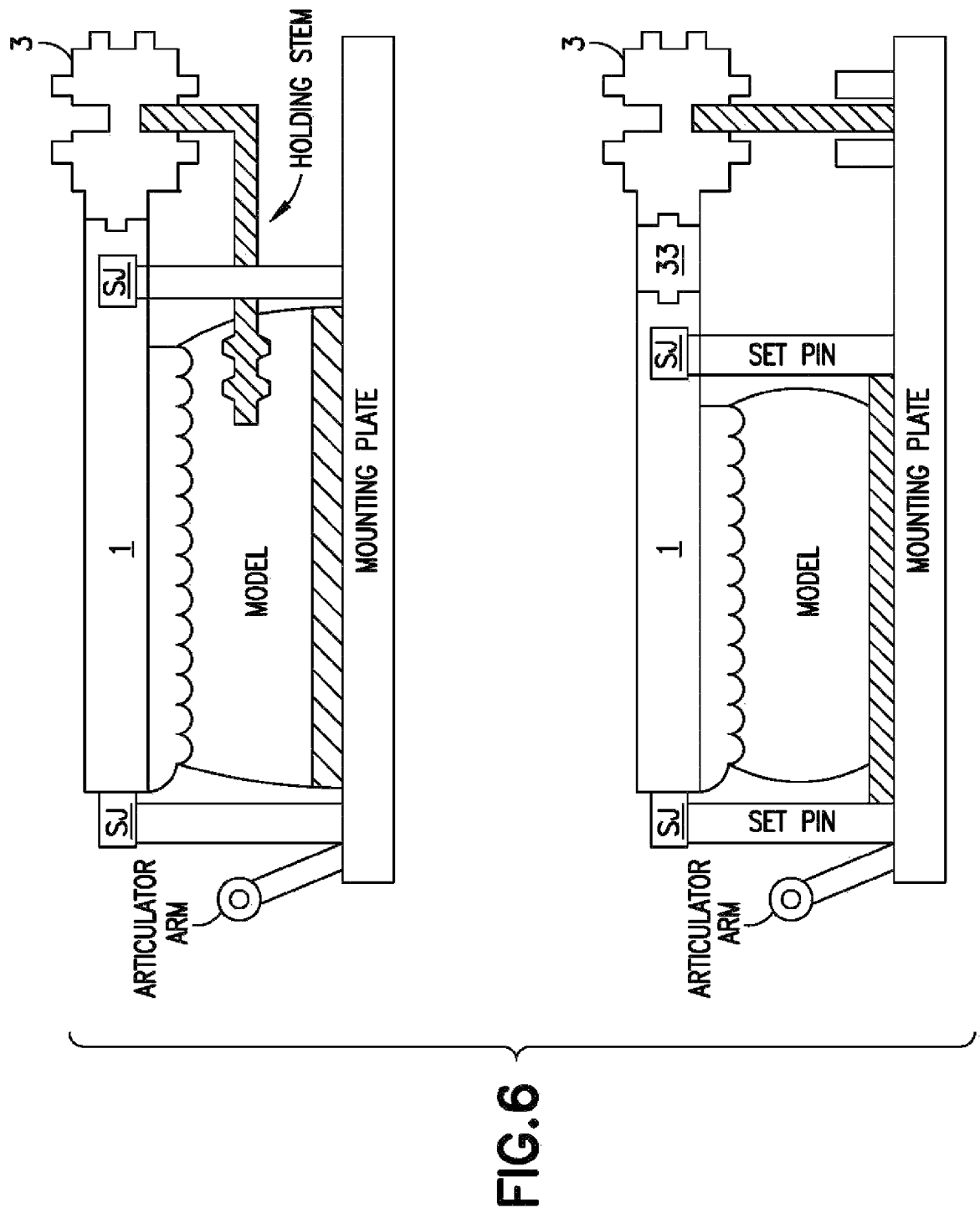
FIG. 6 shows a radiographic template with a dental model on a base plate having an articulator arm according to an example embodiment.

FIGS. 5A through 5G illustrate the use of a radiographic template 1 with a dental model for attachment of the dental model to a base plate of the radiographic template with the transfer of the identical position of the removable SKD 3 to the baseplate so that a desktop scanner can be utilized to scan the dental cast for merger with the CT data set. FIG. 5A shows the radiographic template 1 with set joints SJ attached thereto for mounting the radiographic template 1. A CAD/CAM milled or dental plaster model is applied to the radiographic template 1, as shown in FIG. 5B. The radiographic template 1 is mounted on a mounted plate with set pins SP attached at the set joints SJ and to the mounting plate as shown is FIG. 5C. The dental cast and SKD 3 are transferred to the mounting plate as shown in FIG. 5D, and the SKD 3 is transferred to a SKD mount on the mounting plate such that the SKD 3 is in the same position with respect to the teeth on the mounting plate as when the negative impression was formed in the radiographic template 1. The radiographic template 1 has the SKD 3 attached via an attachment that allows the SKD handle to be detached and reattached to the base plate exactly as it previously related to the dentition. The holding stem is inserted into an opening 13 in the SKD 3 as shown in FIG. 5E to support the SKD 3 in the same position with respect to the teeth on the mounting plate as when the negative impression was formed in the radiographic template. Accordingly, the set pins SP and set joints SJ may be removed from the mounting plate, as shown in FIG. 5F. FIG. 5G shows a top-down view of the radiographic template 1 and the SKD 3 with the set joints SJ attached thereto for mounting on the mounting plate. The dental cast on the mounting plate may be optically scanned, and the optically scanned data is registered with CT scanned data as described above with respect to example embodiments. Accordingly, the SKD 3 may be transferred in the exact position that it was in relation to the dentition for optical scanning. The dental model can thus be scanned instead of the dental impression if particular tooth anatomy that would preclude an accurate optical scan of the dental impression exists. This optical scan of the dental model may be utilized to merge the dental model into the CT scan data, which incorporates processes from US Publication No. 2009/0113714. The scanning of a plaster dental cast or CAD/CAM dental model for the topographic anatomy of the teeth and surrounding structures, as well as the SKD 3, may thus be performed in the exact same orientation as in the CT scan when the radiographic template 1 was held within the mouth of the patient. The mounting base plate may be part of a prefabricated dental articulator that is also utilized for laser scanning of the dental cast and scan body topography, as shown FIG. 6. For example, the mounting plate may have an articulator arm attached thereto for articulation of the dental cast on the mounting plate. The articulator arm may be fixed or adjustable.

Figure 7:
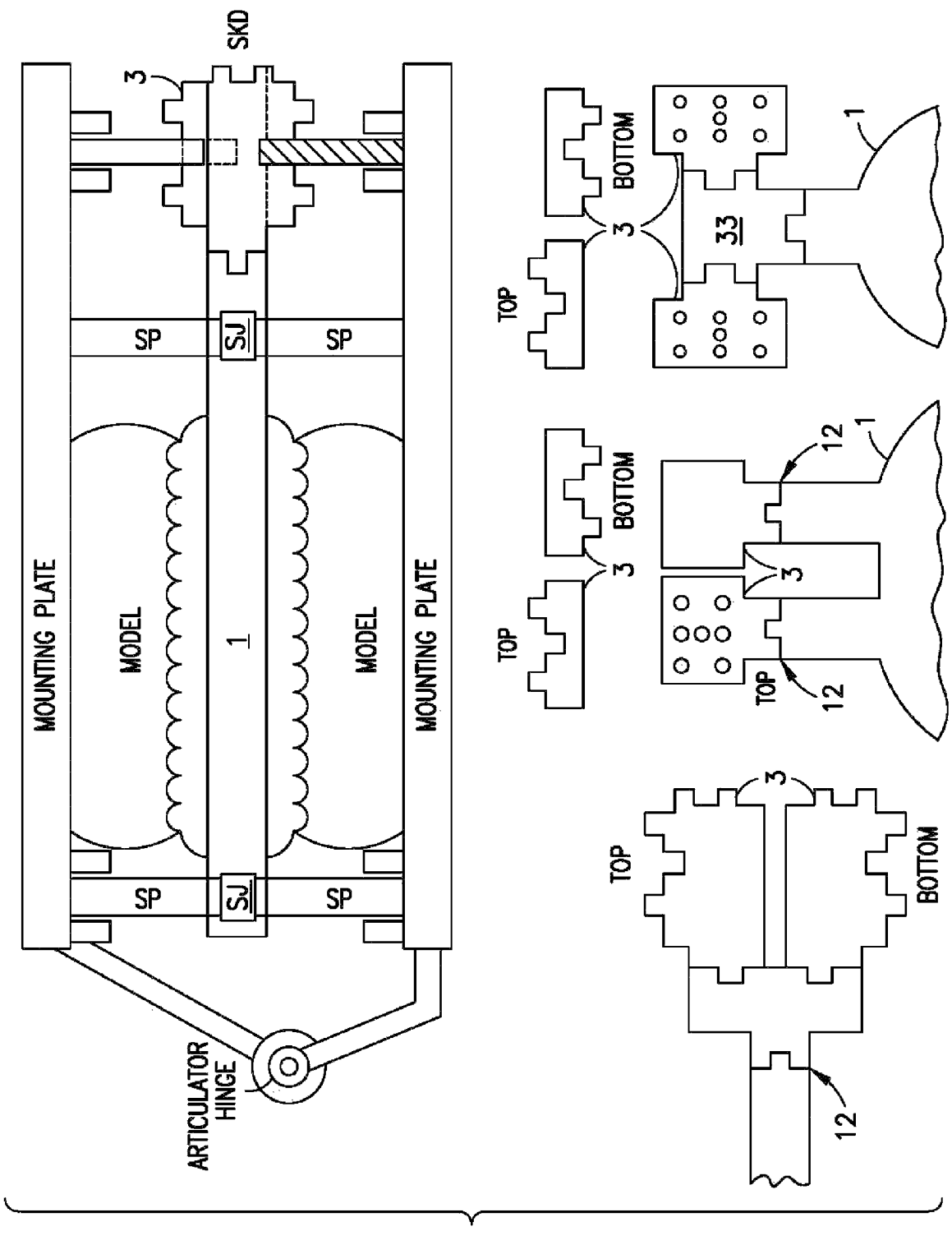
FIG. 7 shows a radiographic template with a dental model of each of the upper jaw and the lower jaw of patient for transfer to individual mounting base plates which are articulable together according to an example embodiment.

If the radiographic template 1 is a triple tray, the models and scan body of each of the upper jaw and the lower jaw may be transferred to an individual mounting base plate, which can be articulated together by a standard dental articulating hinge, as shown in FIG. 7. The physical plaster casts or CAD/CAM manufactured dental models may thus be articulated for reference, as well as used to verify virtual planning, with further modification of the casts or models depending on the dental treatment in progress. The plaster or CAD/CAM dental models are created for optical scanning because it is not always possible to optically scan a dental impression due to the anatomy of the teeth and the subsequent form of the dental impression material due to undercuts and, therefore, it may not be possible to acquire a complete anatomic topography. Dental models scanned according to various well-known dental model scanning processes, such as, those used by Geodyme, LAVA, Etkon and Everest, avoid these difficulties associated with the scanning of impressions and provide for a scan covering the complete anatomic topography.

Another example embodiment of the present invention provides for the fabrication of custom radiographic templates and custom dental impression trays. The custom templates or trays can be formed by a custom tray radiographic appliance on a plaster cast or from a CAD/CAM dental model by a technician for use with an SKD which is modular and removable from the tray or template. The custom trays may include at least three fiducial radiographic radiodense markers 2, and preferably six fiducial radiographic radiodense markers 2. The custom tray appliance or template may also be fabricated with a CAD/CAM manufacturing process from an optical scan of the teeth intra-orally by methods, such as, CEREC, CADENT and others, with the removable SKD 3 being prefabricated and attached to the radiographic template separately after fabrication of the custom template. The custom tray or radiographic template is more customized to the anatomy of a particular patient than a standardized dental impression tray and, thus, allows for a better impression because patients will often have undercuts in their dentoalveolar anatomy or skeletal malformations of their dentoalveolar anatomy. The custom tray may be modular so that other aspects of the dental treatment of a patient can be incorporated in the custom tray, such as, the pick-up of dental implant transfer coping, a CAD/CAM dental bridge, a CAD/CAM temporary bridge with barium impregnation for highlighting in the CT scan, a split cast impressioning for incorporation of tissue loading in cases where there is hyperplastic or hyperplastic gingival, or an orthodontic aligner modular part.

A custom tray or radiographic template may be created in an oral cavity of a patient using cold or light cured materials. A light cured material, e.g., INTERRA manufactured by Dentsply, is formed from a light curable prefabricated horseshoe shaped acrylic that is shaped in the mouth as it is placed over the dental arch of the patient and pressed by finger pressure to obtain an impression of the occlusal surfaces of the teeth and the creation of a flange on the palate, lingual or buccal aspects, and light cured. The light cured material thus creates a highly accurate impression tray or radiographic template by using the dentition of the patient and avoids the inaccuracies of a plaster cast or CAD/CAM model for fabrication. After the light curable material is light cured, a removable SKD 3 is attached to the light cured material serving as the radiographic template 1, which has an intermediate joint 12 so that the SKD 3 is removable, as shown in FIG. 1. Acrylic denture teeth can also be added to the custom light cured radiographic template 1. The light cured radiographic template 1 includes at least 3 fiducial radiographic radiodense markers 2, and preferably six fiducial radiographic radiodense markers 2. A wash of polyvinylsiloxane may be used to take an impression with the custom light cured radiographic template/impression tray so that a complete tooth anatomy and associated soft tissues is obtained for optical scanning and creation of a 3D image to be integrated with the CT scan data after the patient has been CT scanned with the appliance in his or her mouth.

A further example embodiment of the present invention provides a standardized impression tray for a single arch, a dental quadrant, or a "Triple Tray" that is customized by the use of INTERRA material so that a hard acrylic negative impression of the teeth may be obtained. The standardized impression tray thus becomes a customized radiographic template with gutta percha or other fiducial markers together with the removable SKD 3 for forming a polyvinylsiloxone or polyether wash impression to gain a total impression of the tooth undercuts and associated soft tissues.

While the description of the custom and standardized trays disclosed herein describe the SKD 3 as a handle that connects to the SKD 3 to the radiographic template 1, example embodiments are not limited thereto, and there can be other forms of custom and standardized trays that comprise parts other than handles that incorporate attachments for the SKD 3, scanbody or scanbodies. It is a further advantage of the light cured composite material custom radiographic appliance/impression tray or template including a removable handle scanbody SKD that the tray or template may be made the same day that a CBCT scan is obtained, thus saving considerable time and expense for both the patient and the dentist. Furthermore, there is considerable savings for the custom template over a laboratory fabricated template, because INTERRA material is very inexpensive.

A further advantage of a removable scanbody SKD handle end for registration of optical scan data to CT data according to example embodiments is that the removable SKD 3 is not be covered with impression material which might obscure the fiducial markers 2 incorporated into the tray portion of the radiographic template 1. Moreover, depending on the type of CT scan being utilized, whether a medical grade Helical CT scan or a Cone Beam CT (CBCT) scan, the removable SKD 3 may be selected or changed depending on the level of radiation used by the scanning machine. In machines using a lower dose radiation, a less dense material may be utilized for the SKD 3 to ensure a better image of the removable SKD 3, and in machines that use higher dose radiation, a more dense material may be utilized for the SKD 3 to avoid the lack of density needed for recognition of the scanbody SKD 3 by the processing software. Lower dose CBCT machines may thus be used to provide manufacturing of the surgical template through the 3D scan optical image data set. A reduced dosage of radiation from CT and CBCT scanners for the patient is thus achieved. Furthermore, the removable SKD 3 is reusable as opposed to the disposable element of the tray/template 1 which holds the polysiloxane or polyether impression material, or INTERRA material, or other impression or curable hard, soft, or semi-hard dental impression or malleable materials. The tray portion or custom radiographic appliance portion can also be made in a modular method as taught in US Patent Publication Nos. 20060291968 and 20090113714, which allow for the incorporation of different functional elements and the radiographic template to be turned into a custom surgical template, a dental prosthetic insertion jig, a template for transferring a CAD CAM milled overdenture or fixed prosthetic bar, a temporary or final CAD/CAM milled dental prosthesis, a orthodontic aligner modular part, or other medical device for the treatment of neurologic disorders or jaw fractures.

A still further example embodiment of the present invention relates to extrapolation of bone thickness for the incorporation of a 2D x-ray image, such as a periapical radiograph, by using a modular method of radiographic guide fabrication, e.g., as taught by U.S. Publication No. 2006/0291968. A modular part or section that extends over the edentulous ridge that contains a series of bores that allow probing of the modular section of the radiographic guide that is situated over the edentulous region of the jaw is created. The modular part or section is incorporated into the custom radiographic guide or template 1 to provide a mapping guide template that, after probing, is removed and replaced with a part or section that represents a crown and includes the radiographic film or digital x-ray sensor holder x-ray of the patient and the radiographic template guide so that the prosthetic plan can be coordinated with the local bone anatomy. The need for a plaster cast and the creation of a separate mapping appliance is thus avoided. The bores are placed in a standard fashion to allow for the coordination of the probing depths of the gingiva so as to create an outline of the bone width that would not be otherwise be available from a 2D image. A CAD file for a modular part may contain a spline cut through the radiographic template that corresponds to the underlying central occlusal fossae. The modular part of the radiographic template guide comprises, after the surgical planning, the modular drill guide part inserted therein to create the drilling template. The probing data is uploaded into the software program which correlates the probing data to the modular part and determines the thickness of the underlying jaw bone, which avoids the need for CT scanning and thus reduces radiation exposure of the patient. A reduced radiation exposure of the patient may also be achieved by using lower dose Cone Beam CT scanners in which, with the combined use of both the optical 3D scan and CT scan data sets, the robust image of the radiographic template in modular or non-modular form, with an appliance that has a removable scanbody SKD for obtaining an adequate image of the bone anatomy for the determination of a dental implant trajectory, the optical scan data allows adequate imaging of the dentition and virtual CAD/CAM fabrication of a surgical template. Certain machines, for example, the KODAK 9000 or Vatch/Suni devices, are smaller field of view Cone Beam CT scan machines that allow such procedures.

A modular template allows the incorporation of fiducial radiographic radiodense markers 2 into the modular section that is within the smaller field of view and which can be removed and scanned separately at a higher dose of radiation so as to capture the data of the modular section with sufficient density of Hounsfield units to allow that data set to be registered and integrated into the visual model. The modular section may be a standardized template with standardized semi-precision interlocks that allow the repeatable insertion of the modular part or section within the framework of the custom or standardized tray or radiographic template scan appliance 1. If the modular part is a standardized template, the modular part may be stored as a CAD file within the processing software, which allows the modular part in the cases of general low dose radiation, such as, a Sirona Gallileos (which does not have enough KV to create a sufficiently dense image of an acrylic or plastic scan appliance), to be standardized and, therefore, inserted into the software by matching of the SKD of the template or a shape of known dimensions virtually inserted into the template, to allow the modular part of the custom or standardized impression tray or radiographic appliance to be identified and then manipulated by the processing software and matched and incorporated into the overall framework of the appliance. The fabrication of a modular drill guide incorporating the planned dental implant trajectory or trajectories may thus be fabricated by rapid printing, rapid prototyping or CAD/CAM milling, and a metal drill sleeve is inserted into the modular part to create a modular drill guide part for insertion into the radiographic template or impression tray for use as a surgical template for the surgical procedure. The modular section further provides for the creation of CAD/CAM temporary dental prosthetic parts with standardized interlocks to allow the prosthetic parts to be inserted into the custom or standardized appliance framework guideway to be used as a jig for insertion of a prosthetic device at a time of dental implant placement. A plurality of modular parts may be created for the above templates, which can be single jaw devices, or combined as upper and lower jaw custom or standardized impression tray radiographic appliances. As a dual upper and lower custom radiographic appliance or standardized impression tray, the templates may be in a single piece, for example, a triple tray, or detachable for ease of insertion and removal.

The custom radiographic template and standardized impression tray radiographic template appliances, which use a modular or removable SKD, may have various different versions and forms. As stated above, the removable SKD 3 allows the SKD scan body 3 to be transferred to a cast or CAD/CAM dental model. Stone may be poured into the custom radiographic template or standardized impression tray radiographic template to create the dental cast, or the trays may have a plaster dental cast separately poured or a CAD/CAM milled model inserted into the radiographic template or impression tray radiographic template which is attached to the baseplate. Holding stems placed into the plaster case or the CAD/CAM model, or attached to the baseplate, allow the SKD 3 to be transferred to the dental cast or CAD/CAM model, which may be attached by additional plaster or acrylic depending on the material of the model, or attached directly to the base plate. A radiographic template which is a dual handled version which comprises two handles may also be embodied as a single handle with two detachable SKDs 3 attached thereto.

If the template has a modular form, it may be desirable to pull a temporary bridge that may be CAD/CAM fabricated with the impression so that a model is created with the temporary bridge or permanent bridge attached thereto when, for example, it is necessary to recolor the crown, to repair the crown, or to join the crown to other prosthetic parts, whether fixed or removable. The removable SKD 3 may be part of the undersurface or tissue side of the temporary bridge so that when the standardized impression tray radiographic template guide is optically scanned, the SKD 3 on the undersurface of the CAD/CAM bridge is acquired for merging with the scan data and located correctly onto the CAD/CAM milled model. As there are many manufacturers of CAD/CAM milled temporary or permanent crowns, the .stl files of these manufacturers are codified on the SKD 3 on the undersurface of the bridge pontic area and allow a particular software package to incorporate the CAD .stl file from a different manufacturer into the virtual model of the patient, thus allowing a surgical planning software that has an open or closed platform to integrate any other CAD/CAM dental prosthetic manufacturing software into the planning of the dental implant which may come from a variety of dental implant manufacturers and for which a library of implant shapes and sizes can be included and matched with any manufacturer of CAD/CAM crowns or other dental prosthetic parts. Accordingly, a dentist or a dental laboratory can choose which dental implant or dental prosthetic parts to utilize for a particular patient. One advantage of creating a modular radiographic template is that the modular template allows the incorporation of both a dental implant surgical drill guide module and dental prosthetic module parts to be both virtually planned and clinically implemented for the patient. The SKD 3 attached either to the undersurface of the template or as an extension from the crown of the template is used to identify exactly which CAD/CAM manufacturer the SKD 3 came from, and by extension, a CAD file for that particular crown can be obtained from a library or interface with that manufacturer's software.

A modular custom radiographic template or standardized impression tray radiographic template may be a "triple tray" with upper and lower jaw impressions and, in occlusion, the plaster dental casts or CAD/CAM milled models within the appliance may be attached to base plates that have standardized articulating hinges to create an articulated upper and lower jaw model, as shown in FIG. 7, which is useful for performing various of laboratory procedures and verifying a virtual articulated occlusion. The various laboratory procedures may include the preparation of a surgical drill guide for dental implant surgery and the creation of a variety of dental prosthetic parts, such as, conventional crowns, bridges, orthodontic appliances, and removable prosthetic appliances. The triple tray may be formed to allow articulation such that the upper and lower parts are attached and the impressions may be separated and then joined together again. The articulator may also be of the adjustable and semi-adjustable types, for example, a Panadent, so that the condylar position may be verified and transferred to the appliance to establish the patient's Centric Occlusion/Centric Relation positions and/or to establish and correlate the positions to the virtual integrated CT/optical scan data to provide a verification/correlation with the TMJ function and dental occlusion of the patient. Comprehensive restorative dentistry with the integration of various other dental specialty treatments may be managed within the same virtual planning environment.

Figure 3A:
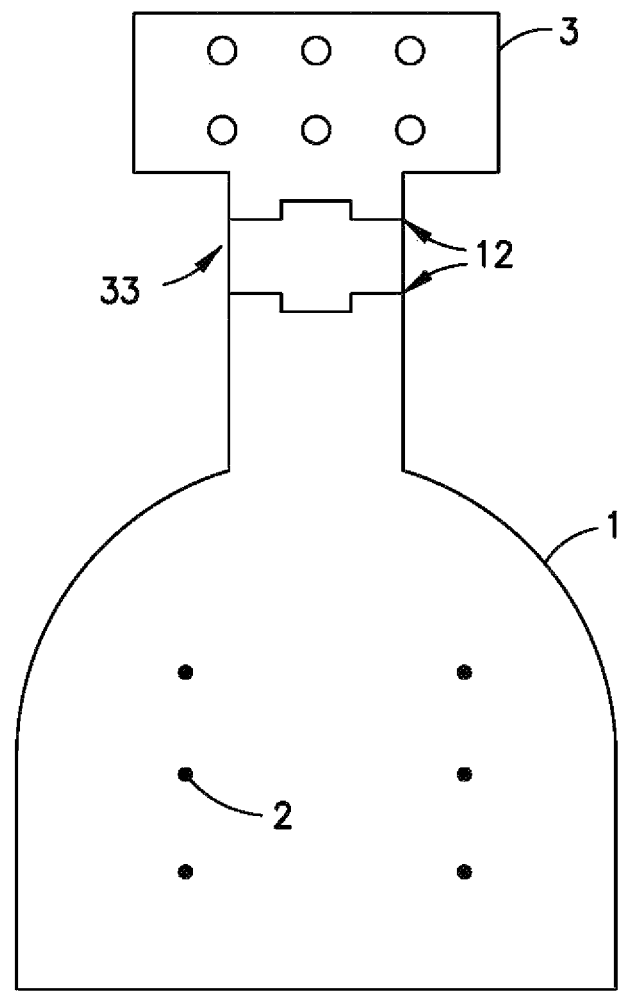
FIG. 3A shows a radiographic template comprising a handle extension for attachment of a SKD according to an example embodiment.
Figure 3B:
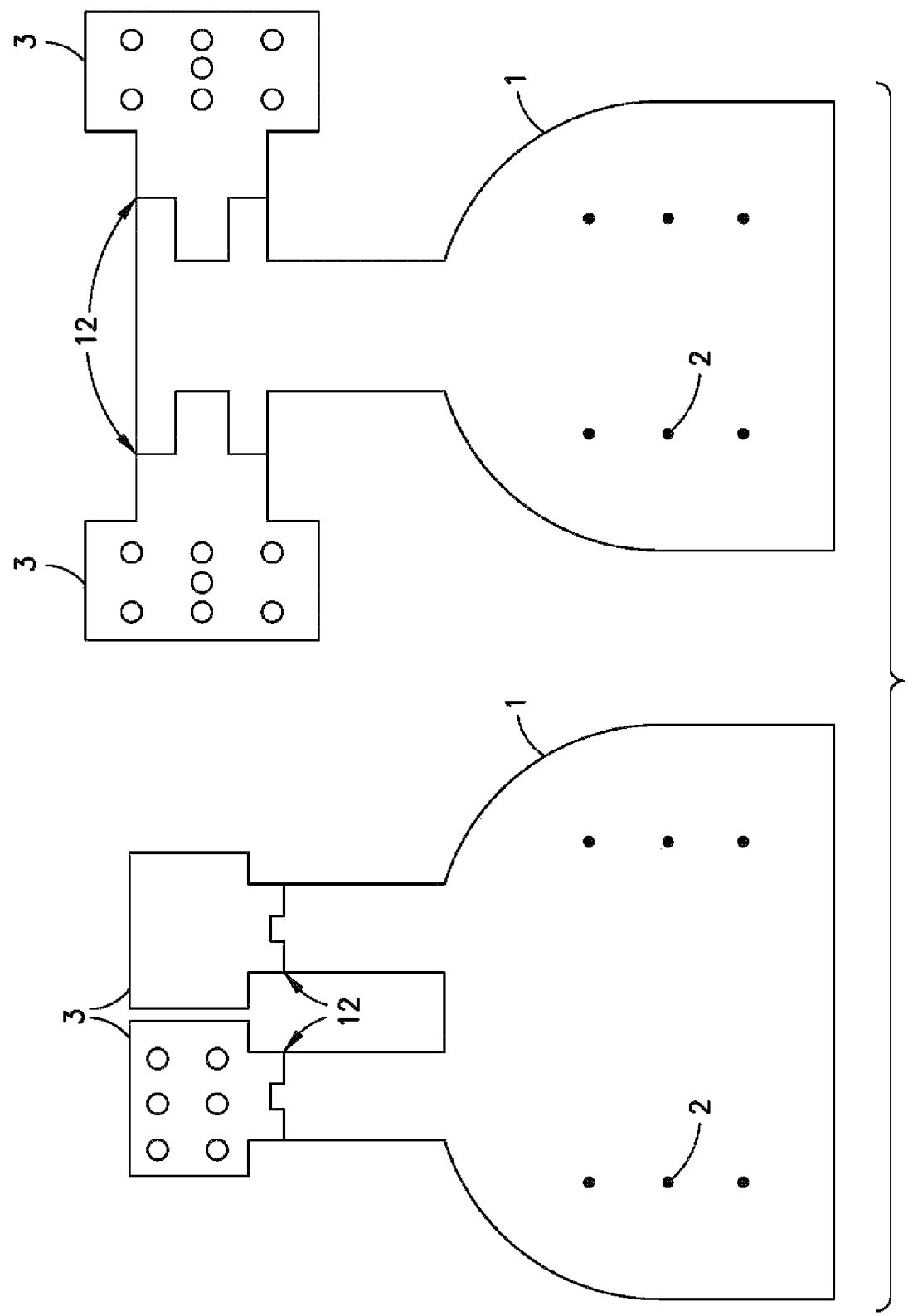
FIG. 3B shows radiographic templates comprising dual removable SKDs according to example embodiments.

Another advantage of the detachable or removable SKD 3 is that the SKD 3 may be configured to protrude from the mouth of the patient away from the teeth which may contain dental restorations so that scatter artifacts are prevented from obscuring the SKD 3. Depending on the number of teeth with metallic restorations, the individual patient anatomy, and the presence of other hardware, such as, titanium bone plates from other reconstructive operations, the radiographic template 1 may comprise one or more additional removable parts 33, as shown in FIG. 3A, to extend the SKD 3 further out of the mouth longitudinally or vertically from the radiographic template 1, but still remain within the confines of a scan window, to further reduce the scatter artifacts which may obscure the scanbody SKD 3 and create registration or matching problems when attempting to register the CT and optical data sets.

If a standardized impression tray radiographic template is utilized, because of the location of the SKD 3 on the handle, a CAD file, which may be embedded within the software, may allow the recognition of the tray, fiducial or scanbody parts so that even in the presence of scatter artifacts the fiducial markers can be located and registration of the CT scan and 3D scan optical data can still be merged.

Placement of gutta percha or other standardized fiducial shapes 2 made of various radiodense materials is incorporated within a standardized impression tray radiographic template 1 separate from the removable SKD 3. Other types of radiographic fiducial markers may be placed within the impression tray, whether the tray is a custom tray or a standardized tray, in addition to the removable SKD 3 in the handle. By separating the fiducial markers 2 from the SKD 3 by extending the SKD 3 from the mouth as a handle, scatter artifacts that occur from the fiducial markers and obscure the SKD 3 are reduced. Separate handles may be created by attaching the SKD 3 as a first handle and the fiducial markers 2 on another separate divergent handle that adequately separates the SKD 3 from the fiducial makers 2 to prevent scatter artifacts from the fiducial markers from obscuring the SKD 3. It is also possible for the removable scanbody SKD 3 to contain the radiodense fiducial markers as well. This configuration is particularly advantageous for patients with large amounts of metal containing dental restorations, or patients who also have considerable jaw hardware, such as, bone plates that are related to maxillofacial reconstructive surgery for cancer, trauma or other developmental or congenital deformities.

After the data acquisition by a CT scan of the patient acquired with a custom radiographic template or a standardized impression tray radiographic template 1, the CT and optical data sets are registered/merged. If a standardized impression tray radiographic template comprises a removable handle scanbody SKD 3 with a polvinylsiloxone impression, it is not necessary to scan the template or appliance alone, i.e., on its own outside the patient's mouth, because a form of the template 1 may be stored as a CAD file. If a custom radiographic template is used, the custom radiographic template needs to be scanned separately on its own and the data set therefrom merged with the CT scan of the patient and the custom radiographic appliance. It is possible that when using a modular type of radiographic template that the SKD 3 is part of the modular part that is inserted virtually within the virtual temporary dental prosthesis either as part of the interlocks or on the undersurface of a pontic such that the SKD 3 is incorporated within the temporary or permanent CAD/CAM prosthesis to be inserted into the radiographic template. If scatter artifacts are present when the CT scan is performed with the radiographic template in the mouth such that the SKD 3 is obscured in the data, the SKD 3 is known within the processing software as a CAD file and the location of the SKD 3 is known so that the SKD 3 can be located within the CT scan data to allow registration of the CT and radiographic template data sets, whether or not the radiographic template is scanned separately in the case of a custom radiographic template or a standardized impression tray radiographic template. By having the CAD file of a standardized form of the SKD 3 and/or the impression template stored, the amount of radiation necessary for the scanning of the patient may be decreased because it is no longer necessary to scan the template or appliance separately. For example, limited window CBCT scanners that obtain images of a section of the jaw may store the CAD file of the standardized template and modular scan body so that the standardized template and modular scan body may be superimposed and a reduced dose of radiation delivered to the patient. This reduction in radiation dosage is also feasible when using a modular custom radiographic template or standardized impression tray radiographic template, because the modular section may be stored as a CAD file with the SKD incorporated therewithin so that the dental implant trajectory may be planned in the bone data set images and the surgical guide fabricated in the modular part which interlocks back into the radiographic template so that a surgical template is created, or a non-modular total surgical template printed, which incorporates the modular section within the total guide framework.

In the merger of the data sets according to example embodiments, the integration of the CT scan data has an accuracy of 0.3-0.5 mm, whereas the optical 3D scan data has an accuracy to within 10-30 microns. The incorporation of the optical scan data set thus allows the highly accurate CAD/CAM manufacturing of surgical templates, radiographic guides, dental prosthetics (whether fixed or removable) and other medical purpose devices. The scanbody SKD CAD file may also be CAD/CAM milled so that the modular removable scanbody SKD handle end may be incorporated into a standardized radiographic guide with a male to female attachment/interlock that is customized in modular parts by the software by using CAD files of known templates for modular sections of a radiographic template that incorporates, as CAD/CAM milled temporary or permanent dental prosthetic parts, orthodontic movement related parts for aligners, or other medical related devices. Accordingly, fiducial markers 2 containing the radiodense material need not be separately applied but, rather, are formed during the manufacturing process of the radiographic template 1. Furthermore, it is contemplated that there may be changes in the future of radiodense material different from the standard or custom tray material so that there does not have to be a change in the manufacturing of the standardized or custom tray material.

Figure 8:
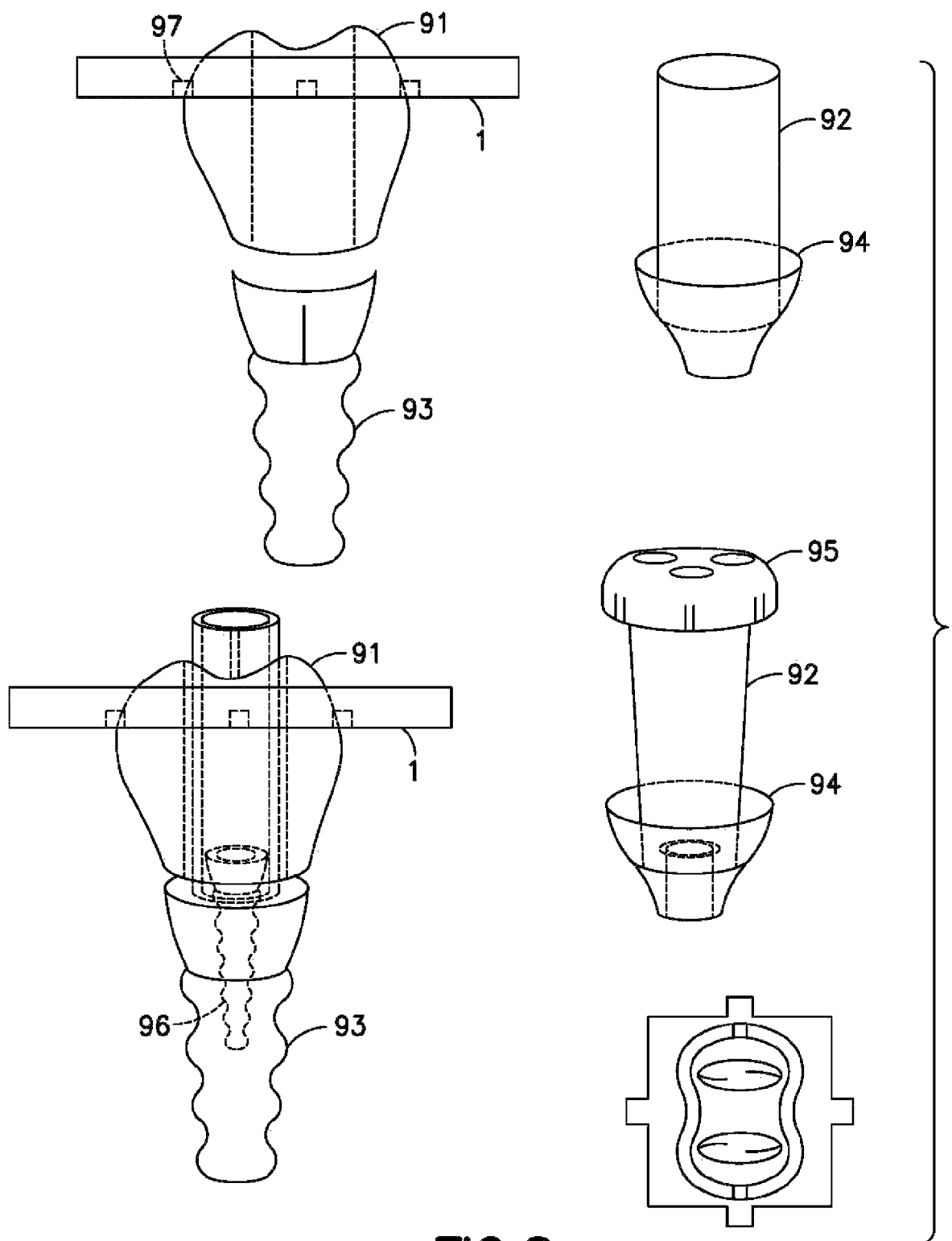
FIG. 8 shows an example dental implant according to an example embodiment.

A further example embodiment is directed to a modular method of creating a CAD/CAM milled crown to be inserted onto the dental implant if the bone is less dense type II or III bone that may not allow the planned dental implant final position to be planned as precisely. FIG. 8 shows an example dental implant according to an example embodiment. A modular surgical drill template may be used for the insertion of a temporary CAD/CAM milled crown 91 with a post on a dental implant 93. As the implant is inserted into the bone, e.g., using a method disclosed in US Publication No. 2006/0291968, which is incorporated herein by reference in its entirety, in a modular method with a modular fabricated drill guide, it may be necessary to turn the implant 93 several turns deeper into the bone so that the implant 93 finally engages and locks into a final position in the bone, which precludes the placement of the CAD/CAM milled crown 91 at the time of dental implant placement. An alternative is to have a CAD/CAM milled crown 91 that will have an opening in the center that accommodates a prefabricated post 92, which can be straight or angled. The post comprises a widened base that extends into a cup 94 form so that when the CAD/CAM milled crown 91 is inserted onto the post 92, it will be attached by resin that is either cold or light cured. The cup 94 catches any flowing resin and prevents the resin from getting onto the bone or under the soft tissue or an undesirable aspect of the base of the post 92. The post 92 may have a cap with a Biomet 3i Encode or Straumann Scan Body type of surface attached, which may be a snap-on that allows either an optical scan or traditional impression so that the data or model can be sent to a dental implant company such as Biomet 3i to scan the model and create a custom final post and crown which is inserted after a period of healing. The cup 94 of the post 92 that catches the flowing resin may be trimmed to create a correctly contoured temporary crown. A screw 96 attaches the dental implant 93 to the post 92. The radiographic template 1 is attached to the crown 91 by supports 97. The modular drill template may also act as a jig if the CAD/CAM milled temporary crown has interlocking attachments that fit into the modular drill template framework and allow the modular drill template gateway to act as a jig for the crown so that the crown is placed in the planned and correct position to the post. Once the crown is placed, the cap 95 may also be placed, and another optical scan or traditional impression that relates the final dental implant position to the planned final CAD/CAM milled abutment or the crown may be obtained. The temporary CAD/CAM milled crown may be utilized as an orthodontic anchorage device that is planned into the case based on the integrated CT and optical scan virtual model. By having a modular surgical template created from the standardized impression tray radiographic template, CAD files of known modular parts can be incorporated into prosthetic solutions, such as, clinical cases where the bone is less dense and the final position of the dental implant is not determinable by a planning function of the software, and abutment solutions based on a known position of the CAD/CAM milled crown within the final surgical template and the use of such modified UCLA type abutments for securing the temporary crown to the dental implant may also be incorporated.

After the custom radiographic template or standardized impression tray radiographic template data sets are obtained from the CT and 3D optical scans, the data is uploaded within the software and computer processing may take place via specific algorithms to match the data sets via surface to surface, contour to contour, or fiducial marker to fiducial marker methods so that an integrated CT and optical scan virtual 3D image of the patient is created for treatment planning for the creation of a surgical template, temporary or permanent dental restoration, orthodontic aligner, or other medical use appliance, such as, the insertion of a device into the maxillofacial region, for example, as an electrode in the greater palatine foramen, or the treatment of a jaw fracture.

Example embodiments of the present invention provide for the creation of dental models by sterolithography, rapid printing and rapid prototyping methods. Dental models formed based on virtual models according to example embodiments have more accurate representations of the patient's teeth including undercuts as well as the dental anatomy of tooth roots. The representations of the tooth roots can be colored in a different color than the rest of the dental model. A series of dental models may be produced by rapid prototyping to create a series of orthodontic aligners for a series of planned tooth movements for the correction of various orthodontic malocclusions. This is an improvement over conventional methods utilized by Align Technologies based on U.S. Pat. Nos. 5,975,893, 6,699,037, 6,722,880 and U.S. Publication No. 2010/00167243, which create a CT scan of a dental cast using a CT industrial scanner. These conventional methods manipulate the CT image of the teeth and the undercuts to create stereolithographic models of each stage of the planned orthodontic tooth movement, and the individual stereolithographic models are then utilized to create dental aligners on an industrial scale production line. Example embodiments, however, obviate the need for a creating a dental cast that has to be separately CT scanned and instead use optical scan data of the digital impression, which is merged with the CT scan of the patient and radiographic template and the separate scan of the radiographic template as described above, to create a virtual model of the patient. The data of the virtual model of the patient is used to fabricate a series of dental aligners without the need for creating a dental cast. Furthermore, example embodiments incorporate the dental root anatomy from the CT scan into the virtual model and plan of the patient, which allows the planned series of orthodontic tooth movements to include the root anatomy including virtually modeled interactions of the root anatomy with bone structure and teeth. Accordingly, when the teeth are moved by software manipulation of the virtual model/image of the patient, the tooth movements, whether they are rotational, tipping, bodily movements in the correction of Class I, II, III tooth crowding, Class I, II, III overjet and overbite discrepancies, combinations of using cut outs in the aligners for Class II and III elastics, or orthodontic brackets for elastic traction, tooth attachments with particular shapes that promote rotation, extrusion, tipping, or bodily movements are considered and virtually modeled. Knowledge of root anatomy can also affect the desired velocity of movement and pattern of movement in order to avoid collision between roots in the process of tooth movement by the planned biomechanical movement of the aligners. It is well understood from dental anatomy studies and CT data concerning tooth roots that there is considerable variation in the pattern of tooth roots that cannot be estimated only by extrapolation from the longitudinal axis of teeth as taught by US Publication No. 2010/0167243. The incorporation of CT data allows more precise knowledge of tooth root anatomy into this type of removable aligner treatment for orthodontic malocclusion. The integration of the CT data and optical scan data of the tooth crown anatomy including the undercuts allows a more precise dental model to be created in which the teeth are represented by accuracy to within 100 microns or less in and the bone anatomy is represented by millimeter level accuracy in the virtual model. Accordingly, a superior aligner that incorporates the CT data of the root anatomy into the biomechanical model of planned orthodontic tooth movements can be fabricated based on the virtual model and planning. It is also possible that with the accumulation of a database of treated cases to create a database, from the virtual models of patients, of common root anatomy patterns that coincide with different anatomic tooth forms and classifications of dental malocclusion such as Class I, II and III. The creation of such a database also facilitates the ability to treat more surgical cases with aligners as there is a greater understanding of the complete dental anatomy and bony anatomy of the maxillomandibular dysplasia.

Direct printing of aligners based on virtual models is achievable by using rapid printing, rapid prototyping technologies as a digital subtraction of the scanned radiographic appliance into the correct form of an aligner or the application of virtual material onto the dental model to create an aligner that is made of a malleable material with adequate flexibility to fit over the undercuts of teeth.

Orthodontic aligners fabricated according to example embodiments may also incorporate planning for dental implants and the creation of combined orthodontic aligners with a surgical drill guide template for the placement of dental implants based on the planned final orthodontic position of teeth and the planned location and trajectory of a dental implant. In the series of orthodontic aligner treatments, the orthodontic aligner may be used as a drill guide for the planned placement of Temporary Orthodontic Anchorage Devices (TADS) which may be part of elastic traction, hybrid aligner and fixed banded orthodontic treatment, and surgical cases where TADS of varying sizes can be used for surgical correction of dentofacial deformities/maxillomandibular dysplasia.

The integrated CT and optical data set is also useful for the creation of dental implant drilling templates that use the planned dental prosthesis as a guide for the planned trajectory of the dental implant as opposed to simply relying on the anatomy of the surfaces of adjacent teeth as in the U.S. Pat. No. 6,319,006. In this way a virtual model of the patient can be created in which the radiographic template will be converted into a surgical drilling template that may be created by either rapid manufacturing, rapid printing or CAD/CAM milling. The virtual model also provides for the creation of drilling templates that are bone based and sit on the bone.

Further example embodiments of the present invention include various modular forms of manufacturing for combining optical scan data with CT scan data. For example, a modular radiographic template 1 may be created in which an SKD 3 interlocks by semiprecision attachment or other types of attachments to a modular part 4 including the fiducial markers 2 of the modular radiographic template 1, which is also interlocked via semiprecision attachments into radiographic template framework 5 to create the total radiographic template 1. The modular part 4 may be, for example, a temporary bridge prosthesis that has been CAD/CAM milled and is attached to the radiographic template framework 5 so as to incorporate a final temporary prosthesis and, by extension, a shape of the final prosthesis into the CT scan data so as to provide the correct prosthetic information for use in treatment planning of the dental implant trajectory or trajectories for the creation of a surgical drill template.

Figure 10:
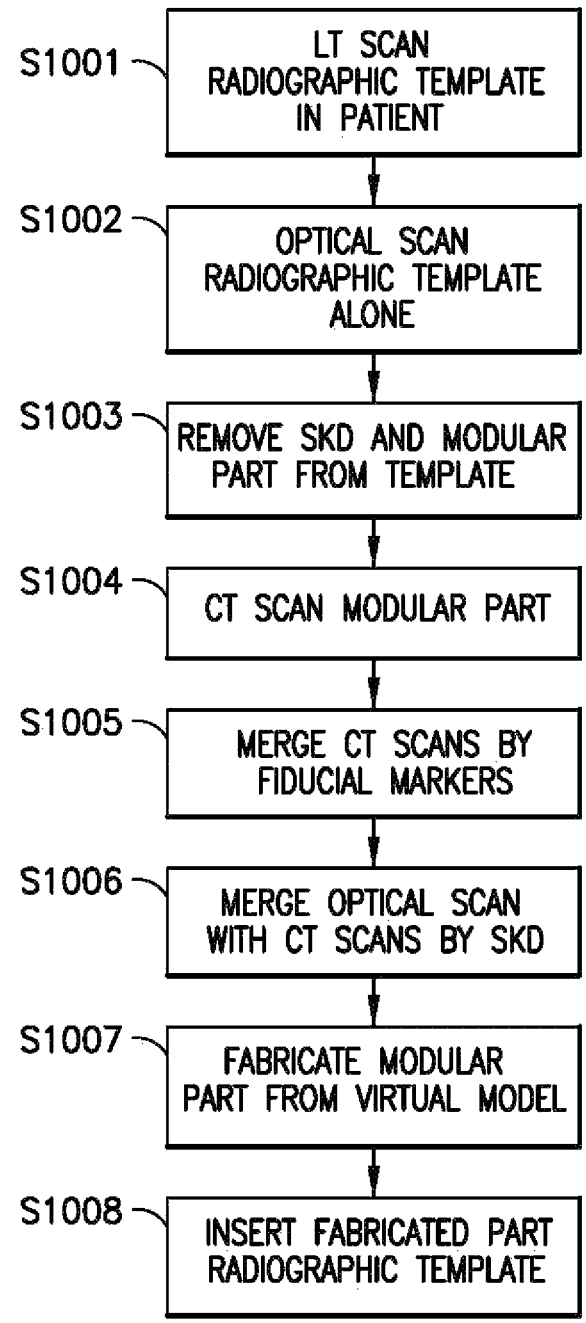
FIG. 10 is a flow chart showing a method for producing from a modular template an artifact corrected image according to an example embodiment.

FIG. 10 is a flow chart showing a method for producing from a modular template an artifact corrected image which includes the registration of data from a CT scan and data from an optical scan according to an example embodiment. A CT scan is performed of the patient with the modular radiographic template 1 in the patient's mouth at S1001. The modular radiographic template 1 can be made of a malleable material, such as, dental acrylic or a polyvinylsiloxane or polyether impression made with the radiographic template, which can be of a standardized form for different sized mouths e.g., small, medium, and large sizes. The radiographic template is removed from the patient, and an optical scan of the total modular radiographic template 1 is created using a desktop scanner or hand held scanner in a dentist's office or at a dental laboratory at S1002. The interlocked SKD 3 and modular part 4 are removed from the total radiographic template 1 at S1003, and the modular part 4 is CT scanned separately at S1004. The CT scanned data sets of the patient and total radiographic template 1 and the modular part 4 alone are merged and registered based on the radiographic/fiducial markers 2 at S1005, and a separate registration and merger of the optical scan data is created so as to create an integrated CT scan and optical scan virtual model of the patient based on the SKD 3 at S1006. Planning for the dental implant trajectory is performed and a drill guide template modular part 6 is fabricated by rapid printing/rapid prototyping/CAD/CAM milling with insertion of drilling sleeves at S1007 based on the virtual model, and inserted at back into radiographic template framework 5 in place of the modular part 4 at S1008. If a polyvinylsiloxane or polyether impression material is utilized, the material can be removed for the insertion of the modular drill guide part 6 into the radiographic template framework 5 for clinical use. Alternatively, the optically scanned model may be merged with a virtual model of the planned temporary bridge obtained via virtual crown planning optical scan software systems, such as, hand held Lava, E4D, iTero, or desktop scanners, such as, Lava, Etkon, Everest, dental wings, to create a surgical drill template via rapid printing, rapid prototyping or CAD/CAM milling and having the accuracy of the fit of the occlusal surfaces from the optical scan of the impression and the CT scan data of the bony anatomy. Accordingly, a modular method of fabricating a surgical drill template can be achieved in a strictly virtual space with the fabrication of the surgical drill template. It is also possible that by utilizing an optical scan of the patient's dentition by a hand held scanner, a radiographic template in whole or modular form can be created for the CT scan and that same data set can be utilized through the integrated merger of the CT scan and optical scan data of the radiographic template to create a dental implant surgical drill template. The same data sets can also be integrated with a planned orthodontic aligner so that if there is a combined orthodontic treatment and dental implant treatment, coordination between these different treatment aspects of the patient can be planned by a single practitioner or communicated between different dental practitioners who may be generalists or specialists. Such planning could be further incorporated and integrated into dental practice management systems for the total management of such combined cases within a dental office or offices in coordination with dental laboratories.

A further example embodiment of the present invention provides for the insertion of an electrode through the greater palatine foramen of a patient into the vicinity of the sphenopalatine gangion (SGG) also known as the nasopalatine ganglion (NPG) for the modulation of electrofrequency to cause vasodilation of the cerebral vasculature in patients suffering from stroke or dementia as disclosed U.S. Pat. Nos. 7,120, 489, 7,729,759, 7,561,919, 7,640,062. The integration of the CT scan of the patient and radiographic template containing the SKD and the separate CT scan of the total template or the modular part of the template merged via registration of the optical scan of the radiographic template provides for the creation of a surgical template based on the virtual model for the insertion of the electrode via the greater palatine foramen. Accordingly, the electrode may be inserted into the patient without needing to surgically open the gum of the patient.

Figure 9:
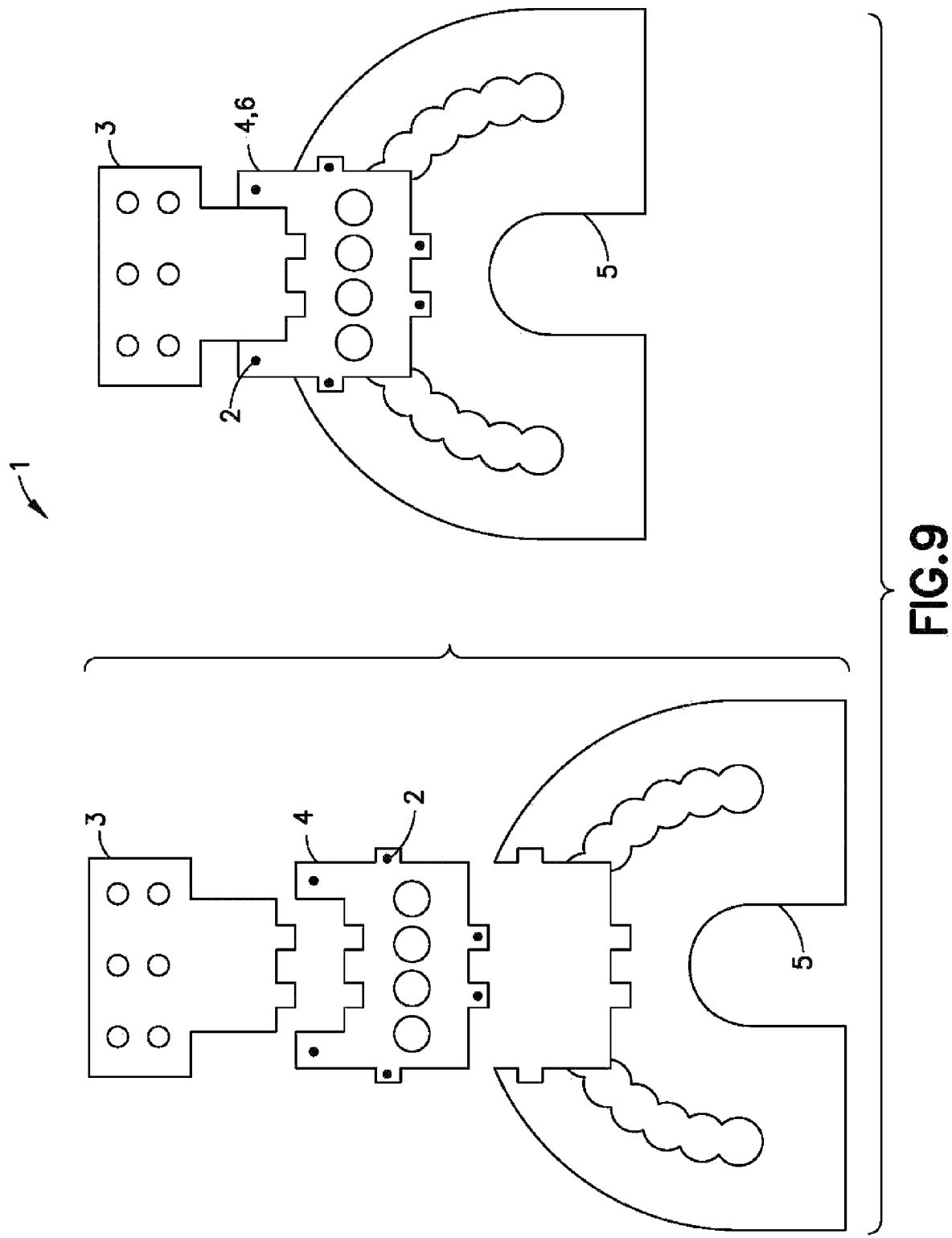
FIG. 9 shows a radiographic template for taking an impression of the upper and lower arches of a patient in a single bite according to an example embodiment.

FIG. 9 shows a radiographic template 1 for taking an impression of the upper and lower arches of a patient in a single bite. Radiographic templates according to example embodiments may be incorporated in a two part process involving the upper and lower jaw arches of a patient to incorporate CT data of the tooth roots in order to create information on the opposing arches in the CT scan data base as disclosed in U.S. Pat. No. 5,975,893, the entire contents of which are incorporated herein by reference. A radiographic template 1 comprising an impression tray that contains polyvinylsiloxane is used to take impressions of each of the upper and lower arches of a patient in a single bite. Radiographic or fiducial markers 2 are placed in the impression tray so that registration of the CT scanned data sets can be performed. A SKD 3 is attached to the handle of the tray so that there is a SKD 3 facing each impression. Therefore, there are two portions of the SKD 3 or separate SKDs 3 on opposing sides of the handle. The dual bite impression tray is CT scanned in the patient's mouth to obtain a first data set. The dual bite impression tray is removed from the patient, placed in a Styrofoam box and scanned in the CT scanner to obtain a second data set. The second data set of the dual impression radiographic guide data set is then registered with first data of the CT scan data of the patient and radiographic guide. Optical scans of each negative impression in the dual bite impression tray are obtained and registered with the CT data set via the respective SKDs 3. Merger of the optical and CT data sets is performed to create a virtual model or models including both the upper and lower arches of the patient. Articulation of the upper and lower arches in the virtual dental model or models is performed and compared to clinical photos submitted by the dentist. Planning of orthodontic movements is performed using the treatment planning software and a series of virtual dental models including the upper and lower arches is created for each stage of orthodontic movement. The planning includes information about the tooth roots in the planning of the orthodontic tooth movements, which improves planning of the forces used for moving each tooth, e.g., rotation, tipping, or bodily movements of each tooth based on known orthodontic biomechanical principles and at a certain velocity over time. Information concerning tooth roots helps to avoid collisions between tooth roots during movements of the teeth in orthodontic treatment and collisions between tooth roots and bone or tooth structures. Furthermore, if a method according to example embodiments is widely utilized and a large number of cases have been performed, information concerning the relationship of crown form to root form and their association with certain case types can be used to aid in the planning and creation of a series of aligners.

Another example embodiment provides for the creation of a virtual dental model as described above using the CT scan of the patient and a dual aligner or single aligners, a separate scan of the radiographic appliance(s), and merger via registration of the scan appliance for the placement of orthodontic brackets for a fixed orthodontic treatment. The planning software is used to plan the orthodontic treatment and to determine what the final position of the teeth will be and what the associated final orthodontic bracket position should be on each tooth so that brackets are located on the stereolithographic model and an aligner is created that will pick up the orthodontic brackets so that the aligner or appliance cements the orthodontic brackets on the teeth by an indirect technique, for example, as disclosed by U.S. Pat. Nos. 6,976,840 and 7,726,968 and the Cadent method, which does not incorporate CT data or root anatomy into the treatment planning. A hybrid treatment according to example embodiments using this method allows both the indirect placement of orthodontic brackets into desired positions in coordination with removable aligner treatment, as well as the incorporation of TADS.

It is a well-known problem that, as a result of the orthodontic movement of teeth, tooth roots may penetrate the supporting alveolar cortical bone and cause the dehiscence of the bone overlying the root partially and completely. The development of gingival recession at the superior aspect of the root and devitalization at the inferior aspect of the root results from this problem.

In the process of orthodontically applying biomechanical forces on teeth, an orthodontist utilizes different kinds of appliances which can be fixed to the teeth or removable, or a combination of fixed and removable appliances. Depending on the appliance used, the teeth are caused to move in certain directions and at a certain rate. Teeth are able to move through the alveolar bone as a result of the biodynamic process of the periodontal ligaments that attach the tooth root to the bone. When force is placed to move the root forward, pressure is created on the forward moving aspect of the root with resultant osteoclastic activity that resorbs the bone allowing the movement and tension on the back of the root with resultant osteoblastic activity and bone deposition. Depending on the type of movement, there can be variations of tension and pressure along the root surface causing bone resorption and deposition as the tooth is moved to its desired position. If the tooth movement is excessive or does not properly take into account the alveolar bone morphology, penetration of the bony cortices may occur with resultant gingival recession and mucogingival defects. Gingival recession occurs at the superior aspect of the root in the attached gingiva where there is a decrease in the attached gingiva and exposure of the root surface. A mucogingival defect is a more advanced lesion where the attached gingiva is completely receded and only the areolar mucosa remains, which creates a more advanced loss of periodontal attachment and root exposure. A mucogingival defect, with its lack of keratinized gingival, is less cleansable and less resistant to the effects of bacteria in plaque, which causes an inflammatory response that creates a worsening of the periodontal defect and allows the gingival recession and bone dehiscence to deteriorate, which jeopardizes the health of the tooth and can cause a premature loss of the tooth. This is a greater problem in adult orthodontics than in orthodontics in children and adolescents. However, if the orthodontic treatment of children and adolescents is not performed correctly, areas of root perforation or penetration with dehiscence can lead to periodontal disease later in life. Endodontic lesions can also develop as a result of orthodontic tooth movement, which can relate to tooth collisions, overcompression of the periodontal ligament, penetration or perforation of the bony cortices that lead to devitatlization of the tooth with loss of apical vascular supply to the pulp, or development of root resorption.

A removable SKD 3 may be placed in coordination with existing dental implants, temporary dental implants or temporary orthodontic anchorage devices (TADS) so that the SKD does not have to be bonded onto the dentition, but may be easily placed and removed from the implants. The implants, temporary mini-implants or TADS, by providing attachment to the SKD 3, may also be removably attached to a custom or standardized impression tray or template and are another form of removable scanbody handle that may be used for both the CT and optical scanning of the patient, optical scanning of the custom radiographic template or standardized impression tray radiographic template and the fixation of the surgical drill guide template during a surgical procedure to drill the bone and insert the dental implants through the surgical drill guide template which can be total or modular in form. The removable SKD 3 is useful in various methods of dental laboratory procedures for the treatment of transitional cases where various types of permanent and temporary dental implants and TADS are used in the process of removing certain non-restorable non-useful teeth and maintaining other teeth for various strategic reasons, such as temporization, bone maintenance, patient financial considerations, coordination of orthodontics, periodontics, prosthodontics, oral surgery, endodontics, and reconstructive jaw surgery for patients with acquired, developmental or congenital, or pathological deformities and defects, in order to provide comprehensive dental prosthetic rehabilitation.

Figure 11:
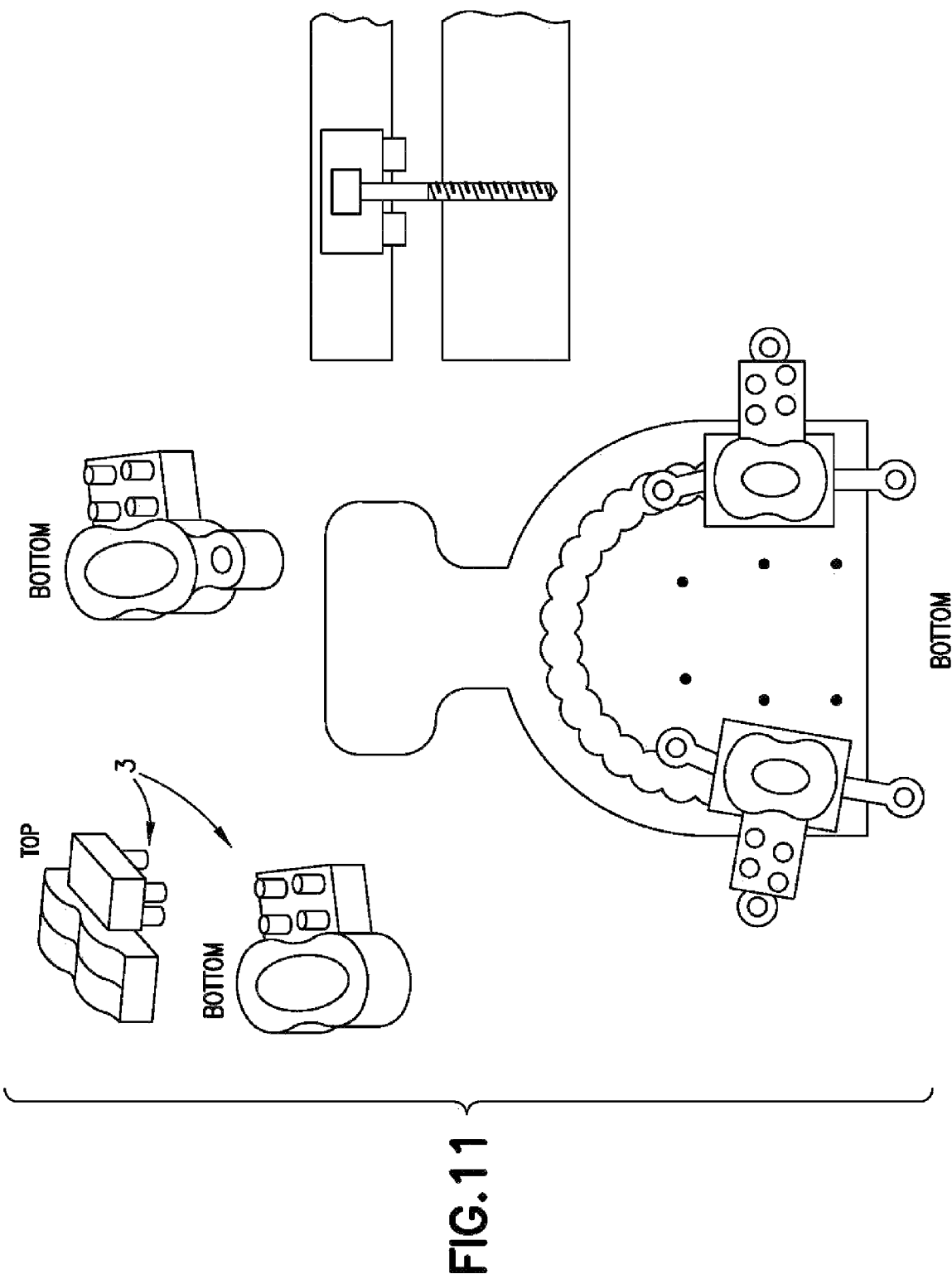
FIG. 11 shows a crown attached to temporary orthodontic anchorage devices (TADS) according to an example embodiment.

The removable SKD 3 may have a shape such that it is easily attached by various types of joints with retentive elements. In the manufacturing of CAD/CAM milled crowns, whether temporary or permanent, the crowns may have the SKD 3 attached to them to allow both the optical and CT registration of the data. The crown can be attached to the custom or standardized radiographic template or impression tray by a modular interlock, or can be picked up in an impression with polyvinylsiloxane or polyether impression material, so that the crown incorporated into the scan appliance. The CAD/CAM crown with the removable SKD 3 thus becomes the removable handle with a scanbody SKD of the appliance. The CAD/CAM milled crowns may have retentive elements incorporated within them so that the crowns can be attached to temporary orthodontic anchorage devices (TADS), temporary mini-implants or permanent implants, as shown in FIG. 11.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A device for use in optical scanning and CT scanning, comprising:
    a radiographic template including a plurality of radio-opaque markers and configured to take an impression of at least one surface of a patient; and
    at least one separate shape of known dimensions (SKD) removably attached to the radiographic template, said at least one SKD serving as a basis for registration of data of a CT scan of the device with data of an optical scan of the device.

2. The device for use in optical scanning and CT scanning of claim 1, wherein the radiographic template further includes a modular section which is removable from the radiographic template.

3. The device for use in optical scanning and CT scanning of claim 1, wherein the at least one SKD includes at least one opening for receiving a holding stem for holding the at least one SKD in an exact same position with respect to surfaces in a model formed from the impression as when the impression of the patient is formed in the radiographic template.

4. The device for use in optical scanning and CT scanning of claim 1, further comprising a male-to-female connection joint removably attaching the at least one SKD to the radiographic template.

5. The device for use in optical scanning and CT scanning of claim 1, wherein the at least one SKD is two or more SKDs.

6. A device for use in optical scanning and CT scanning of claim 1, comprising
    a radiographic template including a plurality of radio-opaque markers and configured to take an impression of at least one surface of a patient;
    at least one shape of known dimensions (SKD) removably attached to the radiographic template, said at least one SKD serving as a basis for registration of data of a CT scan of the device with data of an optical scan of the device; and
    a removable part removably attaching the at least one SKD to the radiographic template and extending the at least one SKD further out of the mouth of the patient longitudinally or vertically from the radiographic template.

7. The device for use in optical scanning and CT scanning of claim 1, further comprising:
    a mounting plate, wherein the at least one SKD is mounted on the mounting plate such that the at least one SKD is in an exact same position with respect to surfaces in a model formed from the impression as when the impression of the patient is formed in the radiographic template, and wherein the SKD is removed from the radiographic template.

8. The device for use in optical scanning and CT scanning of claim 7, wherein the mounting plate comprises an articulator arm configured to articulate the model on the mounting plate.

9. The device for use in optical scanning and CT scanning of claim 8,
    wherein the at least one surface is a first surface and a second surface of the patient,
    wherein the model comprises a model of the first surface and the second surface,
    wherein the at least one SKD is two SKDs,
    wherein the model of the first surface is mounted on a first mounting plate such that a first SKD of the two SKDs is in an exact same position with respect to the first surface of the model as when the impression of the patient is formed in the radiographic template, and wherein the first SKD is removed from the radiographic template, wherein the model of the second surface is mounted on a second mounting plate such that the second SKD of the two SKDs is in an exact same position with respect to the second surface of the model as when the impression of the patient is formed in the radiographic template, and wherein the second SKD is removed from the radiographic template, and wherein the model of the first surface on the first mounting plate and the model of the second surface on the second mounting plate are configured to be articulated together by an articulating hinge attached to the first mounting plate and the second mounting plate.

10. A method for producing a virtual model of a patient, comprising:

removably attaching at least one shape of known dimensions (SKD) to a radiographic template extending the at least one SKD out of a patient's mouth longitudinally or vertically from the radiographic template;

providing the radiographic template including an impression of at least one surface of the patient, the radiographic template having the at least one SKD removably attached thereto;

creating a model from the impression in the radiographic template;

mounting the radiographic template having the at least one SKD attached thereto on at least one mounting plate such that the at least one SKD is transferred to the mounting plate in an exact same position with respect to surfaces in the model as when the impression was formed in the radiographic template; and one of optically scanning and CT scanning the model and the SKD on the mounting plate without the radiographic template.

11. The method for producing a virtual model of a patient of claim 10, further comprising:

inserting a holding stem into an opening in the at least one SKD to support the at least one SKD in the exact same position with respect to the surfaces in the model as when the impression of was formed in the radiographic template.

12. The method for producing a virtual model of a patient of claim 10, further comprising:

placing the radiographic template in contact with the at least one of the first surface and the second surface of said patient, said radiographic template comprising a plurality of radio-opaque markers;

forming the impression of the at least one of the first surface and the second surface by said radiographic template;

performing a first CT scan of said radiographic template and said at least one surface of said patient;

removing said radiographic template from said at least surface of said patient;

performing a second CT scan of said radiographic template apart from said at least one surface of said patient;

merging said first CT scan and said second CT scan based on said plurality of radio-opaque markers to produce an artifact-corrected image;

merging said artifact-corrected image and said optical scan based on said shape of known dimensions to produce the virtual model of said patient.

13. The method for producing a virtual model of a patient of claim 12, wherein the SKD comprises a material selected based on a radiation level of the first CT scan.

14. The method for producing a virtual model of a patient of claim 10, further comprising:

placing the radiographic template in contact with the at least one surface of said patient, said radiographic template comprising a plurality of radio-opaque markers;

forming the impression of the at least one surface by said radiographic template;

performing a first CT scan of said radiographic template and said at least one surface of said patient;

removing said radiographic template from said at least one surface of said patient;

retrieving stored CT scan data of said radiographic template apart from said at least one surface of said patient without performing a CT scan data of said radiographic template apart from said at least one surface of said patient;

merging said first CT scan and said CT scan data based on said plurality of radio-opaque markers to produce an artifact-corrected image;

merging said artifact-corrected image and said optical scan based on said shape of known dimensions to produce the virtual model of said patient.

15. The method for producing a virtual model of a patient of claim 14, wherein the SKD comprises a material selected based on a radiation level of the first CT scan.

16. The method for producing a virtual model of a patient of claim 10, wherein the at least one surface is a first surface and a second surface of the patient, wherein the model comprises a model of the first surface and the second surface, wherein the at least one SKD is two SKDs, wherein the model of the first surface is mounted on a first mounting plate such that a first SKD of the two SKDs is in an exact same position with respect to the first surface of the model as when the impression of the patient is formed in the radiographic template, and wherein the SKD is removed from the radiographic template, wherein the model of the second surface is mounted on a second mounting plate such that the second SKD of the two SKDs is in an exact same position with respect to the second surface of the model as when the impression of the patient is formed in the radiographic template, and wherein the SKD is removed from the radiographic template, and wherein the model of the first surface on the first mounting plate and the model of the second surface on the second mounting plate are configured to be articulated together by an articulating hinge attached to the first mounting plate and the second mounting plate.

17. The method for producing a virtual model of a patient of claim 10, further comprising:

removing the at least one SKD from the radiographic template;

reusing the at least one SKD for scanning with a different radiographic template.

18. The method for producing a virtual model of a patient of claim 10, further comprising:

inserting a modular section, which is removable from the radiographic template, in the radiographic template.

19. The method for producing a virtual model of a patient of claim 10, wherein a removable part removably attaches the at least one SKD to the radiographic template and extends the at least one SKD further out of the mouth of the patient longitudinally or vertically from the radiographic template.

20. The method for producing a virtual model of a patient of claim 10, wherein the at least one SKD comprises two or more SKDs.

21. The method for producing a virtual model of a patient of claim 10, further comprising:

creating a surgical splint for orthognatic surgery based on the optical scan of the model.

* * * * *